United States Patent
Abood et al.

(10) Patent No.: US 9,622,995 B2
(45) Date of Patent: Apr. 18, 2017

(54) TREATMENT OF DISORDERS ASSOCIATED WITH G PROTEIN-COUPLED RECEPTOR 35 (GPR35)

(71) Applicants: TEMPLE UNIVERSITY—OF THE COMMONWEALTH SYSTEM OF HIGHER EDUCATION, Philadelphia, PA (US); DUKE UNIVERSITY, Durham, NC (US); RESEARCH TRIANGLE INSTITUTE, Research Triangle Park, NC (US)

(72) Inventors: Mary E. Abood, Gladwyne, PA (US); Pingwei Zhao, Wynnewood, PA (US); Lawrence S. Barak, Durham, NC (US); Herbert H. Seltzman, Raleigh, NC (US)

(73) Assignees: TEMPLE UNIVERSITY—Of The Commonwealth System of Higher Education, Philadelphia, PA (US); DUKE UNIVERSITY, Durham, NC (US); RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 14/711,355

(22) Filed: May 13, 2015

(65) Prior Publication Data
US 2015/0265561 A1 Sep. 24, 2015

Related U.S. Application Data

(62) Division of application No. 13/386,288, filed as application No. PCT/US2010/041930 on Jul. 14, 2010, now Pat. No. 9,040,583.

(60) Provisional application No. 61/227,647, filed on Jul. 22, 2009.

(51) Int. Cl.
*A61K 31/194* (2006.01)
*A61K 31/191* (2006.01)

(52) U.S. Cl.
CPC .......... *A61K 31/194* (2013.01); *A61K 31/191* (2013.01)

(58) Field of Classification Search
CPC .................................................. A61K 31/194
See application file for complete search history.

(56) References Cited

U.S. PATENT DOCUMENTS

| 4,291,026 A | 9/1981 | Tobkes et al. |
| 6,020,452 A | 2/2000 | Pu et al. |
| 7,153,881 B2 | 12/2006 | Lundstedt et al. |
| 2006/0205967 A1 | 9/2006 | Gallo et al. |
| 2008/0293812 A1 | 11/2008 | Gallo et al. |

FOREIGN PATENT DOCUMENTS

| WO | WO-2005/085867 | 9/2005 |
| WO | WO-2005/119252 | 12/2005 |

OTHER PUBLICATIONS

Cosi, et al., (2008) "The antinociceptive effects of L-kynurenine in the writhing test may be mediated by interaction kynurenic acid-GPR35" (program No. 267.1/FF7), in Washington D.C.: *Society for Neuroscience Meeting*, 2008 Online, Washington DC.
Guo, et al., "Inhibition of N-Type Calcium Channels by Activation of GPR35, an Orphan Receptor, Heterologously Expressed in Rat Sympathetic Neurons", *The Journal of Pharmacology and Experimental Therapeutics*, vol. 324, No. 1, 342-351, 2008.
Ohshiro, et al., "GPR35 is a functional receptor in rat dorsal root ganglion neurons", *Biochemical and Biophysical Research Communications* 365 (2008) 344-348.
Okada, et al., "Propionibacterium freudenreichii component 1.4-dihydroxy-2-naphthoic acid (DHNA) attenuates dextran sodium sulphate induced colitis by modulation of bacterial flora and lymphocyte homing", *Gut* 2006: 55: 681-688.
Okumura, et al., "Cloning of a G-protein-coupled receptor that shows an activity to transform NIH3T3 cells and is expressed in gastric cancer cells", *Cancer Sci*, Feb. 2004, vol. 95, No. 2, 131-135.
Ryberg, et al., "The orphan receptor GPR55 is a novel cannabinoid receptor", *British Journal of Pharmacology* (2007) 152, 1092-1101.
Shrimpton, et al., "Molecular delineation of deletions on 2q37.3 in three cases with an Albright hereditary osteodystrophy-like phenotype", *Clin Genet* 2004: 66: 537-544.
Taniguchi, et al., "5-Nitro-2-(3-Phenylpropylamino)benzoic Acid is a GPR35 Agonist", *Pharmacology* 2008: 82: 245-249.
Taniguchi, et al., "Zaprinast, a well-known cyclic guanosine monophosphate-specific phosphodiesterase inhibitor, is an agonist for GPR35", *FEBS Letters* 580 (2006) 5003-5008.
Wang, et al., "Kynurenic Acid as a Ligand for Orphan G Protein-coupled Receptor GPR35", *The Journal of Biological Chemistry*, vol. 281, No. 31, pp. 22021-22028, 2006.
Van Duinen et al. "Hereditary cerebral hemorrhage with amyloidosis in patients of Dutch origin is related to Alzheimer disease", *Proc. Natl. Sci.*, 1987, vol. 84, pp. 5991-5994.

*Primary Examiner* — Samira Jean-Louis
(74) *Attorney, Agent, or Firm* — Drinker Biddle & Reath LLP

(57) ABSTRACT

Compounds are provided having agonistic activity against G protein-coupled receptor 35 (GPR35). The compounds are useful for providing antinociception, providing neuroprotection in case of stroke or ischemia, or treating gastric inflammation.

6 Claims, 21 Drawing Sheets

Fig. 1

N-terminus
MLSGSRAVPTPHRGSEELLKYMLHSPCVSLTMNGTYNTCGSSDLTWPPAIK  20
GPR35b, 31 aa insert    |→ GPR35a 21  LGFYAYLGVLLVLGLLLNSLALWVFCCRMQQWTETRIYMTNLAVADLCLL  70
         TM1                              TM2

71  CTLPFVLHSLRDTSDTPLCQLSQGIYLTNRYMSISLVTAIAVDRYVAVRH  120
                              TM3

121 PLRARGLRSPRQAAAVCAVLWVLVIGSLVARWLLGIQEGGFCFRSTRHNF  170
                       TM4

171 NSMAFPLLGFYLPLAVVFCSLKVVTALAQRPPTDVGQAEATRKAARMVW  220
              TM5

221 ANLLVFVVCFLPLHVGLTVRLAVGWNACALLETIRRALYITSKLSDANCC  270
            TM6                            TM7

271 LDAICYYYMAKEFQEASALAVAPRAKAHKSQDSLCVTLA
                                          C-terminus Control:
GPR35 cells Pamoic acid 1 μM:
GPR35 cells Pamoic acid 1 µM:
V2R cells Fig. 6C
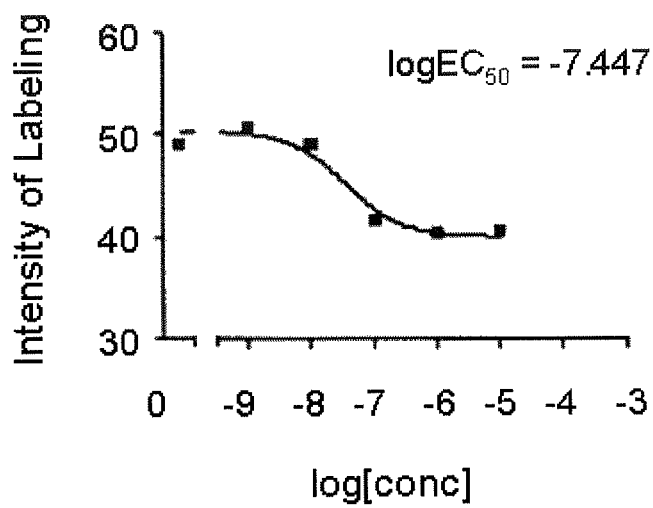
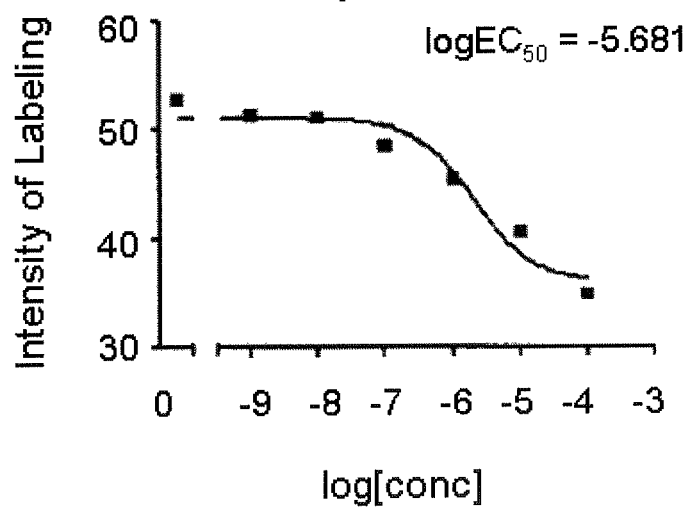

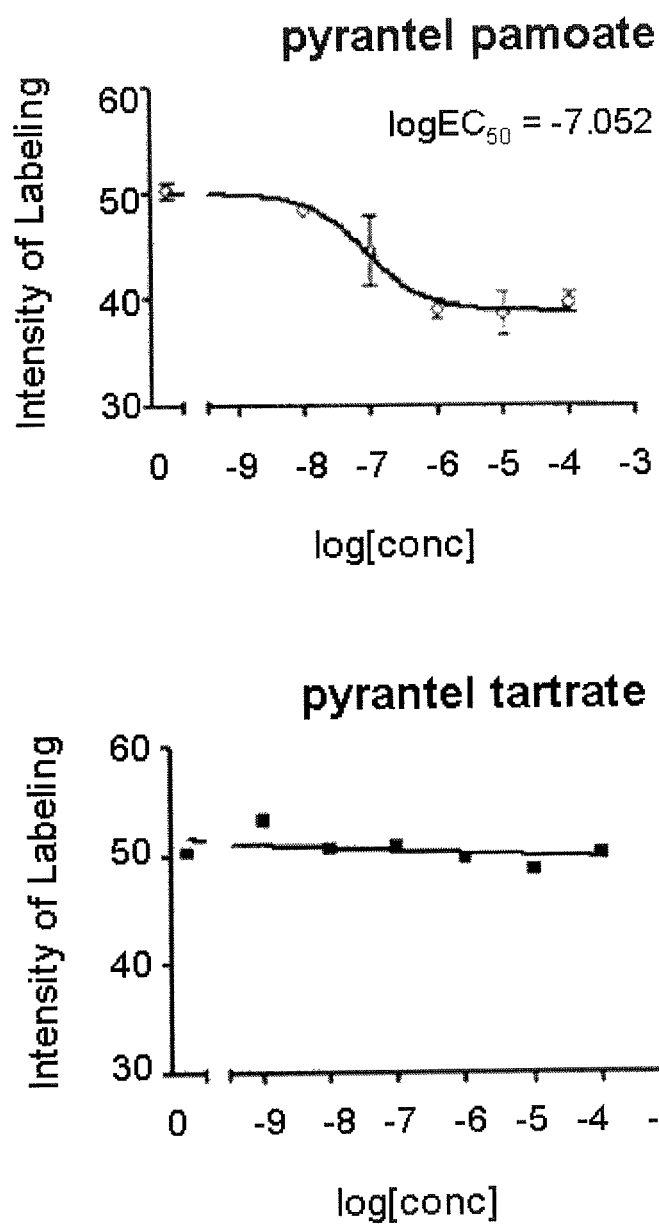

Fig. 7A
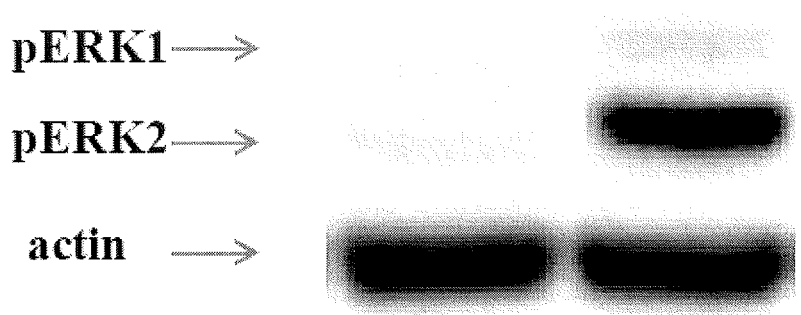
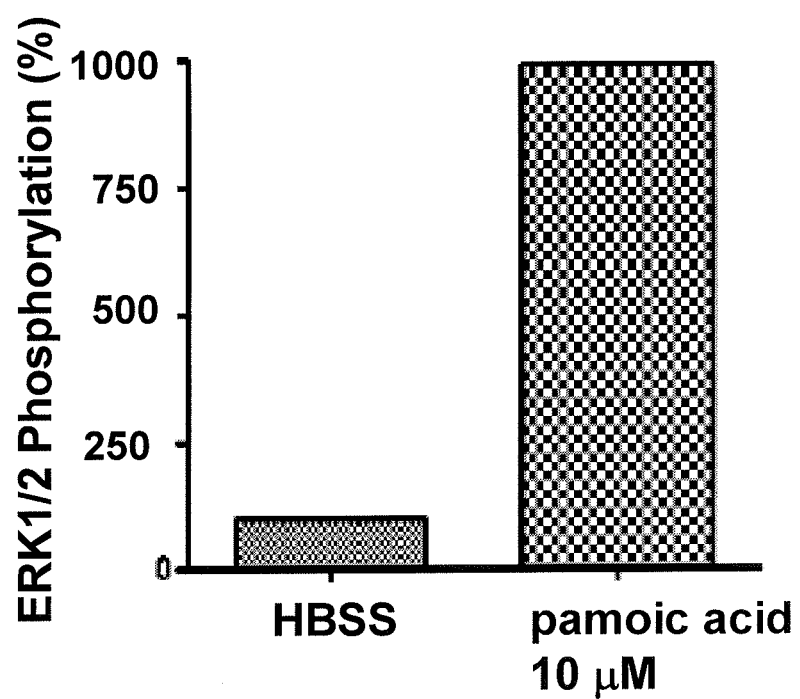

Fig. 7B
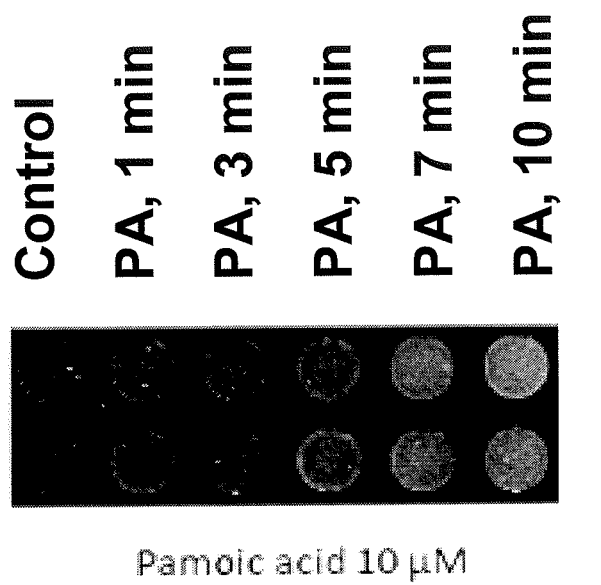
Pamoic acid 10 μM
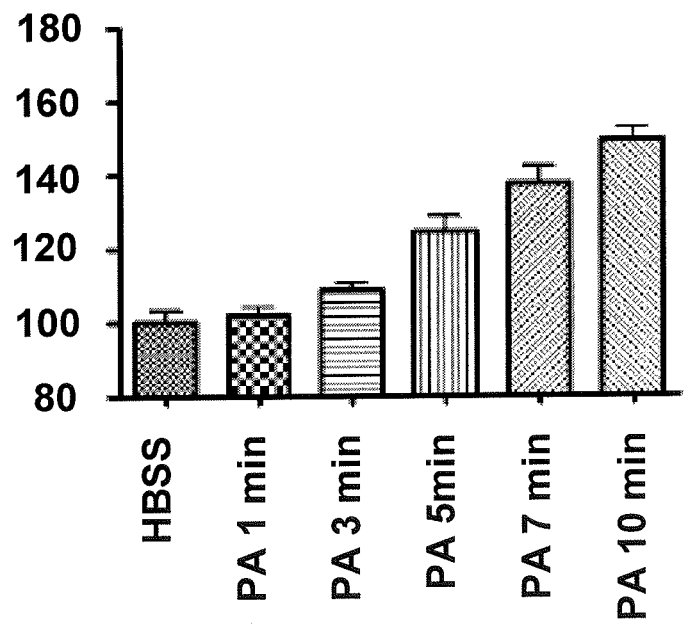

Fig. 11C
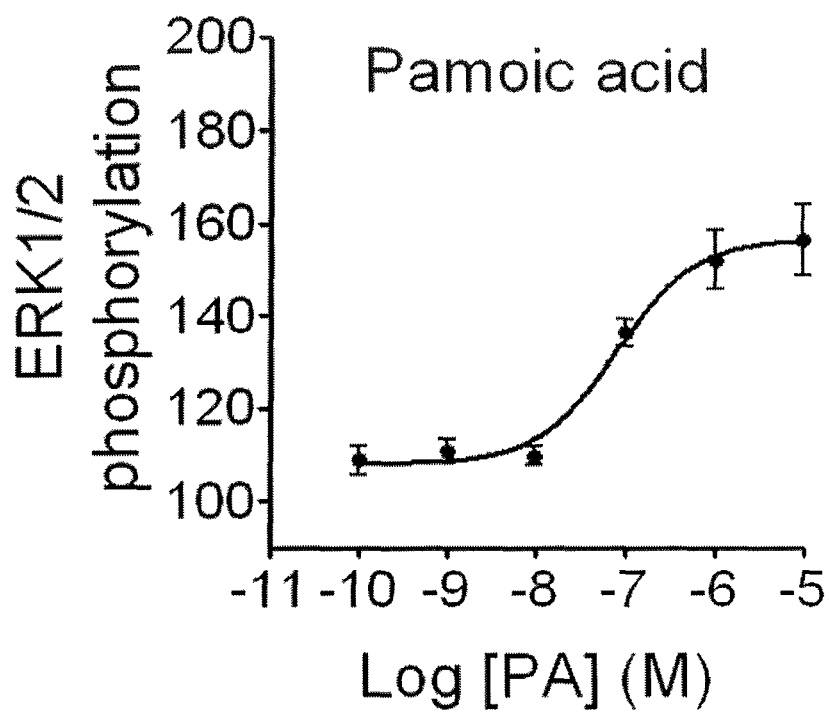
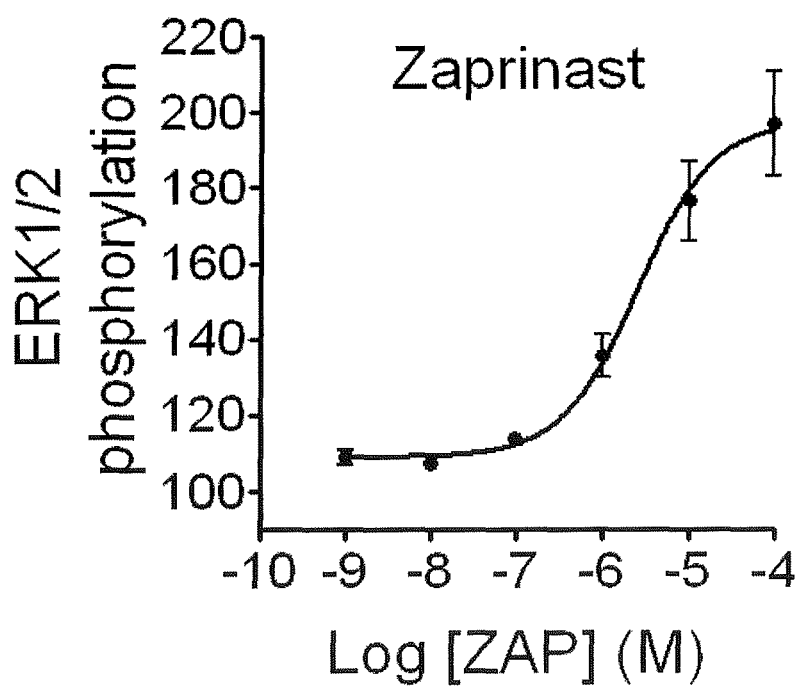

TREATMENT OF DISORDERS ASSOCIATED WITH G PROTEIN-COUPLED RECEPTOR 35 (GPR35)

CROSS-REFERENCE TO RELATED APPLICATIONS

This application is a divisional of U.S. patent application Ser. No. 13/386,288, filed Jan. 20, 2012, issued as U.S. Pat. No. 9,040,583 on May 26, 2016, which is the US national stage of international application PCT/US2010/041930, filed Jul. 14, 2010, which claims the benefit of U.S. Provisional Application No. 61/227,647, filed Jul. 22, 2009, the entire disclosures of which are incorporated herein by reference.

REFERENCE TO GOVERNMENT GRANT

The invention described herein was supported in part by the Government grant number DA 023204, awarded by the National Institutes of Health (U.S. Department of Health and Human Services). The Federal Government may have certain rights in the invention.

SEQUENCE LISTING

The instant application contains a Sequence Listing which has been submitted in ASCII format via EFS-Web and is hereby incorporated by reference in its entirety. Said ASCII copy, created on May 8, 2015, is named 035926_0391_01_US_SeqListing_ST25, and is 11,559 bytes in size.

FIELD OF INVENTION

The invention relates to agonists of G protein-coupled receptor 35 (GPR35) and their use in methods of providing antinociception, providing neuroprotection in case of stroke or ischemia, or treating gastric inflammation in a subject in need thereof.

BACKGROUND OF THE INVENTION

A cellular receptor is a protein molecule that is embedded in the plasma membrane or cytoplasm of a cell, and may bind to a mobile signaling molecule. The molecule that binds to a receptor is called a "ligand", and may be a peptide (such as a neurotransmitter), a hormone, a pharmaceutical drug, or a toxin. When the ligand binds to the receptor, the receptor generally undergoes a conformational change, triggering a cellular response. However, some ligands act solely as antagonists, blocking receptors without inducing any response. Ligand-induced changes in receptors result in physiological changes that ultimately constitute the biological activity of the ligands. Although ligand binding is generally the trigger for receptor activation, some receptors are capable of producing a biological response in the absence of a bound ligand. These receptors are said to have "constitutive activity" or "baseline activity".

Ligands may have different activities with respect to cellular receptor activation and/or inactivation. An agonistic ligand is able to activate the receptor and result in a biological response that is enhanced over the baseline activity of the unbound receptor. Many natural ligands are full agonists. A partially agonistic ligand does not activate the receptor thoroughly, causing responses that are smaller in magnitude compared to those of full agonists. An antagonistic ligand binds to the receptor but does not activate them. This results in receptor blockage, inhibiting the binding of other agonists. An inversely agonistic ligand reduces the activity of receptors by inhibiting their constitutive activity.

G protein-coupled receptors (GPCRs) are also known as seven-transmembrane domain receptors (7TM receptors), heptahelical receptors, serpentine receptor, and G protein-linked receptors (GPLRs). GPCRs comprise a large protein family of transmembrane receptors that sense molecules outside the cell, activating intracellular signal transduction pathways and, ultimately, cellular responses. G protein-coupled receptors are found only in eukaryotes, including yeast, plants, choanoflagellates, and animals. The ligands that bind and activate these receptors include small molecules, peptides, large proteins, pheromones, hormones, and neurotransmitters. G protein-coupled receptors are involved in many diseases, and are the target of approximately one-half of all modern medicinal drugs (Filmore, 2004, Mod. Drug Disc. 24-28).

GPCRs share a common structural motif, having seven sequences of between 22 to 24 hydrophobic amino acids that form α-helices, each of which spans the membrane. Each membrane-spanning segment is identified by number: transmembrane-1 (TM-1), transmembrane-2 (TM-2), transmembrane-3 (TM-3), transmembrane-4 (TM-4), transmembrane-5 (TM-5), transmembrane-6 (TM-6), and transmembrane-7 (TM-7). The transmembrane helices are joined by strands of amino acids between transmembrane-2 and transmembrane-3, transmembrane-4 and transmembrane-5, and transmembrane-6 and transmembrane-7 on the extracellular side of the cell membrane (these are referred to as "extracellular" regions EC-1, EC-2 and EC-3, respectively). The transmembrane helices are also joined by strands of amino acids between transmembrane-1 and transmembrane-2, transmembrane-3 and transmembrane-4, and transmembrane-5 and transmembrane-6 on the intracellular side of the cell membrane (these are referred to as "intracellular" regions IC-1, IC-2 and IC-3, respectively). The C-terminus of the receptor lies in the intracellular space, and the N-terminus of the receptor lies in the extracellular space.

There are several principal signal transduction pathways involving the G-protein coupled receptors, including the cAMP signal pathway and the phosphatidylinositol signal pathway (Gilman, 1987, Ann. Rev. Biochem. 56:615-649). When a ligand binds to the GPCR, a conformational change is triggered in the GPCR, which then acts as a guanine nucleotide exchange factor (GEF). The GPCR may then activate an associated G-protein by exchanging its bound GDP for a GTP. The G-protein α-subunit, with the bound GTP, may then dissociate from the β- and γ-subunits to further affect intracellular signaling proteins or target functional proteins directly depending on the α-subunit type ($G_{\alpha s}$, $G_{\alpha i}$, $G_{\alpha q/11}$, $G_{\alpha 12/13}$).

Excluding odorant receptors, the human genome encodes roughly 350 GPCRs, which have hormones, growth factors, and other endogenous transmitters as ligands. Approximately 150 of the GPCRs found in the human genome have unknown functions. Those GPCRs for which the natural ligand is unknown are referred to as "orphan" receptors.

One of these orphan GPCRs is GPR35. This receptor was first cloned by O'Dowd and coworkers after a screen of a human genomic library (O'Dowd et al, 1998, Genomics 47:310-313). The GPR35 gene contains a single exon that encodes a predicted 309-amino acid protein ("GPR35a" hereafter—SEQ ID NO:1 for amino acid sequence), and is mapped to region 2q37.3 by fluorescence in situ hybridization. Subsequently, the GPR35 gene was identified in a 66-kb interval on chromosome 2 (Horikawa et al., 2000, Nature Genet. 26: 163-175). GPR35 expression was detected in all fetal and adult human tissues examined, with relatively higher levels in adult lung, small intestine, colon, and stomach. Recently, Okumura and coworkers (Okumura et al., 2004, Cancer Sci. 95:131-135) found that GPR35a and an alternatively spliced form of GPR35 (which contains 31 amino acids at the N-terminus of GPR35) are expressed in gastric cancers. The alternatively spliced form of GPR35 is designated GPR35b (SEQ ID NO:2 for amino acid sequence). The amino acid sequence and domains of GPR35a and GPR35b are shown in FIG. 1.

GPR35 is homologous to the P2Y purinergic receptor GPR23, for which the ligand is lysophosphatidic acid, and it shares a 30% identity with the putative cannabinoid receptor GPR55 (Guo et al., 2008, J. Pharmacol. Exp. Ther. 324 (1):342-351; Taniguchi et al., 2006, FEBS Lett. 580 (21): 5003-5008; Johns et al., 2007, Br. J. Pharmacol. 152 (5): 825-31; Ryberg et al., 2007, Br. J. Pharmacol. 152 (7):1092-1101). Preliminary studies of GPR35 by mRNA expression showed that it is expressed predominantly in the immune and gastrointestinal systems with no detection observed in brain tissue (O'Dowd et al, 1998, Genomics 47:310-313). However, recent RT-PCR studies have confirmed the presence of GPR35 in dorsal root ganglion, the cerebellum and brain, and GPR35b was cloned from a human whole brain cDNA library (Guo et al., 2008, J. Pharmacol. Exp. Ther. 324 (1):342-351; Ohshiro et al., 2008, Biochem. Biophys. Res. Commun 365 (2):344-348; Taniguchi et al., 2006, FEBS Lett. 580 (21):5003-5008).

Three compounds—kynurenic acid (2-carboxy-4-hydroxy-quinoline), zaprinast (5-(2-propoxyphenyl)-1H-pyrazolo[4,3-d]pyrimidin-7 (6H)-one), and 5-nitro-2-(3-phenylpropylamino)-benzoic acid (NPPB)—were recently identified as GPR35 agonists (Taniguchi et al., 2006, FEBS Lett. 580 (21):5003-5008; Taniguchi et al., 2008, Pharmacology 82 (4):245-249; Wang et al., 2006, J. Biol. Chem. 281 (31):22021-22028). Kynurenic acid, a metabolite of tryptophan and inhibitor of the ionotropic glutamate receptor, was identified using an intracellular calcium assay that required the co-expression of a mixture of G proteins. Using an Aequorin bioluminescence reporter readout in CHO cells co-transfected with either human, mouse, or rat GPR35, $EC_{50}$ values for receptor activation were determined as 40 μM, 11 μM, and 7 μM respectively (Wang et al., 2006, J. Biol. Chem. 281 (31):22021-22028). Results were confirmed by using a secondary GTPγs membrane binding assay in the absence and presence of pertussis toxin. These measured $EC_{50}$ values are relatively high in comparison to values typically observed for the affinities of endogenous GPCR agonists, which routinely fall in the intermediate to low nanomolar range. As such, a "true" high affinity endogenous ligand that would deorphanize GPR35 remains to be discovered.

There is thus a need to identify potent GPR35 receptor agonists, which may be used to activate the receptor and shed light on the receptor function in different cells and tissues. There is also a need to further characterize the cellular processes controlled and regulated by the GPR35 receptor, and determine which diseases or conditions may be treated by an agonist of this receptor. The present invention addresses and meets these needs.

SUMMARY OF THE INVENTION

The present invention is based on the unexpected discovery that certain 1,1'-binaphthyl and methylene-1,1'-binaphthyl compounds, or their pharmaceutically acceptable salts, are potent agonists of the orphan G protein-coupled receptor GPR35. Binding of these compounds to the GPR35 receptor causes activation of the receptor as judged by three distinct assays: recruitment of β-arrestin to the cell membrane, receptor internalization, and activation of ERK1/2 by phosphorylation. These compounds find use in providing antinociception, providing neuroprotection in case of stroke or ischemia, or treating gastric inflammation in a subject in need thereof.

The pharmaceutical compositions and methods of the invention utilize a compound of Formula (I):

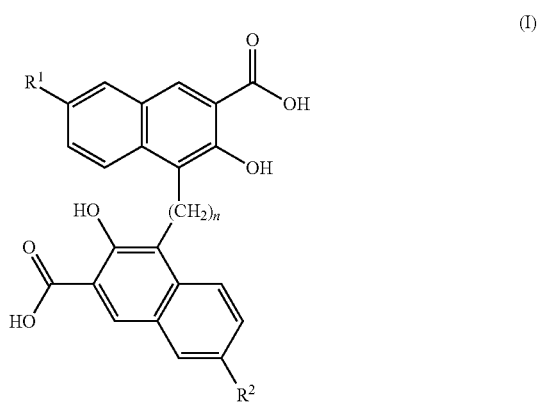

(I)

or a pharmaceutically acceptable salt thereof, wherein:
$R^1$ and $R^2$ are independently H, F, Cl, Br or I; and,
n is 0 or 1.

In one embodiment, $R^1$ is H. In another embodiment, $R^2$ is H. In yet another embodiment, $R^1$ and $R^2$ are the same, e.g., $R^1$ and $R^2$ are both H, or $R^1$ and $R^2$ are both Br. In yet another embodiment, n is 0. In yet another embodiment, n is 1. In yet another embodiment, the compound of Formula (I) is pamoic acid, or a pharmaceutically acceptable salt thereof. In yet another embodiment, the compound of Formula (I) is oxantel pamoate. In yet another embodiment, the compound of Formula (I) is pyrantel pamoate, or a pharmaceutically acceptable salt thereof. In yet another embodiment, the compound of Formula (I) is 7,7'-dibromo-pamoic acid, or a pharmaceutically acceptable salt thereof. In yet another embodiment, the compound of Formula (I) is 1,1'-binaphthyl-2,2'-diol-3,3'-dicarboxylic acid, or a pharmaceutically acceptable salt thereof.

In one embodiment, the pharmaceutically acceptable salt comprises a cationic counterion that is selected from the group consisting of sodium, potassium, calcium, magnesium and ammonium. In another embodiment, the pharmaceutically acceptable salt comprises a cationic counterion that is selected from the group consisting of sodium and potassium.

In one embodiment, the invention is directed to a method of increasing GPR35 function in a cell, wherein the method comprises contacting the cell with an effective amount of a compound of Formula (I) as defined above, or a pharmaceutically acceptable salt thereof. In another embodiment, the invention includes a compound of Formula (I) as defined above, or a therapeutically acceptable salt thereof, for use in increasing GPR35 function in a cell.

In one embodiment, the invention is directed to a method of providing antinociception to a subject in need of such treatment, wherein the method comprises administering to the subject a therapeutically effective amount of a compound of Formula (I) as defined above, or a pharmaceutically acceptable salt thereof, wherein the pharmaceutically acceptable salt comprises a cationic counterion which itself does not provide therapeutically useful antinociception. In another embodiment, the invention includes a pharmaceutical composition comprising a compound of Formula (I) as defined above, or a therapeutically acceptable salt thereof, wherein the pharmaceutically acceptable salt comprises a cationic counterion which itself does not provide therapeutically useful antinociception, for use in providing antinociception to a subject in need thereof.

In one embodiment, the invention includes a method of providing neuroprotection in case of stroke or ischemia to a subject in need of such treatment, wherein the method comprises administering to the subject a therapeutically effective amount of a compound of Formula (I) as defined above, or a pharmaceutically acceptable salt thereof, wherein the pharmaceutically acceptable salt comprises a cationic counterion which itself does not provide therapeutically useful neuroprotection in case of stroke or ischemia. In another embodiment, the invention includes a pharmaceutical composition comprising a compound of Formula (I) as defined above, or a therapeutically acceptable salt thereof, wherein the pharmaceutically acceptable salt comprises a cationic counterion which itself does not provide therapeutically useful neuroprotection in case of stroke or ischemia, for use in providing neuroprotection in case of stroke or ischemia to a subject in need thereof.

In one embodiment, the invention includes a method of treating gastric inflammation in a subject in need of such treatment, wherein the method comprises administering to the subject a therapeutically effective amount of a compound of Formula (I) as defined above, or a pharmaceutically acceptable salt thereof, wherein the pharmaceutically acceptable salt comprises a cationic counterion which itself does not provide therapeutically useful treatment for gastric inflammation. In another embodiment, the invention includes a pharmaceutical composition comprising a compound of Formula (I) or a therapeutically acceptable salt thereof, wherein the pharmaceutically acceptable salt comprises a cationic counterion which itself does not provide therapeutically useful treatment for gastric inflammation, for use in treating gastric inflammation in a subject in need thereof.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DESCRIPTION OF FIGURES

Embodiments of the present invention will now be described, by way of example only, with reference to the attached Figures.

FIG. 1 is a schematic representation of the amino acid sequence of GPR35a (SEQ ID NO:1 for amino acid sequence) and the alternatively spliced form GPR35b (SEQ ID NO:2 for amino acid sequence). Underlined are the 31-amino acid sequence at the N-terminus of GPR35b, as well as the transmembrane domains of GPR35a and GPR35b.

FIG. 3A corresponds to untreated UGPR35β cells. FIG. 3B corresponds to UGPR35β cells treated with 1 µM pamoic acid. FIG. 3C corresponds to a U2OS cell line containing β-arrestin2-GFP and overexpressed vasopressin receptor (V2R), treated with 1 µM pamoic acid. Fluorescence is seen as bright light spots in the images.

FIG. 4A shows the fluorescence imaging obtained at different concentrations of each tested compound—pamoic acid (PA), zaprinast (ZA) and kynurenic acid (KYNA). FIG. 4B shows the corresponding concentration response curves, derived by analyzing the fluorescence images for the amount of translocated β-arrestin-GFP aggregates.

FIG. 5A shows the immunofluorescence image of untreated UGPR35β cells. FIG. 5B shows the immunofluorescence image of UGPR35β cells treated with pamoic acid. FIG. 5C shows the titration curve derived from quantitating the loss of cell surface receptor (measured as intensity of labeling) as a function of pamoic acid concentration (in log scale). FIG. 5D shows the LI-COR images acquired at different concentrations of pamoic acid.

FIGS. 6A-E show the ligand-induced GPR35 internalization in UGPR35β cells for different ligands. FIG. 6A shows the loss of intensity of labeling of GPR35 receptor (measured by immunofluorescence) with increasing concentrations of zaprinast, kyrurenic acid and oxantel pamoate. FIG. 6B shows the loss of intensity of labeling of GPR35 receptor (measured by immunofluorescence) with increasing concentrations of pamoic acid, pyrantel tartrate and pyrantel pamoate. FIG. 6C shows the corresponding binding curves for ligand-mediated GPR35 internalization, along with calculated $EC_{50}$ values, for pamoic acid and zaprinast. FIG. 6D shows the corresponding binding curves for ligand-mediated GPR35 internalization, along with calculated $EC_{50}$ values, for pyrantel pamoate and pyrantel tartrate. FIG. 6E shows the corresponding binding curves for ligand-mediated GPR35 internalization, along with calculated $EC_{50}$ values, for oxantel pamoate.

FIGS. 7A-C show the pamoic acid-induced activation (phosphorylation) of ERK1/2 in UGPR35β cells. FIG. 7A shows the Western blot analysis and quantitation for untreated cells (left) and cells treated with 10 µM pamoic acid (right). Actin was used to normalize data. FIG. 7B shows the In-Cell Western analysis of cells treated with varying concentrations of pamoic acid. The analysis was performed using a LI-COR infrared imager and the data quantitation was normalized to cell number. FIG. 7C shows the % ERK1/2 activation as a function of the incubation time of the cells with pamoic acid.

FIGS. 11A-C show the agonist-mediated ERK1/2 phosphorylation in U2OS cells expressing GPR35a. FIG. 11A shows the concentration response of ERK1/2 phosphorylation of GPR35a cells treated for 15 minutes with pamoic acid. FIG. 11B shows the In-Cell Western analysis with a LI COR Odyssey infrared imager using 96-well plate. FIG. 11C shows the response curve of ERK1/2 phosphorylation from In-Cell Western analysis (n=3).

DEFINITIONS

Figure 2:
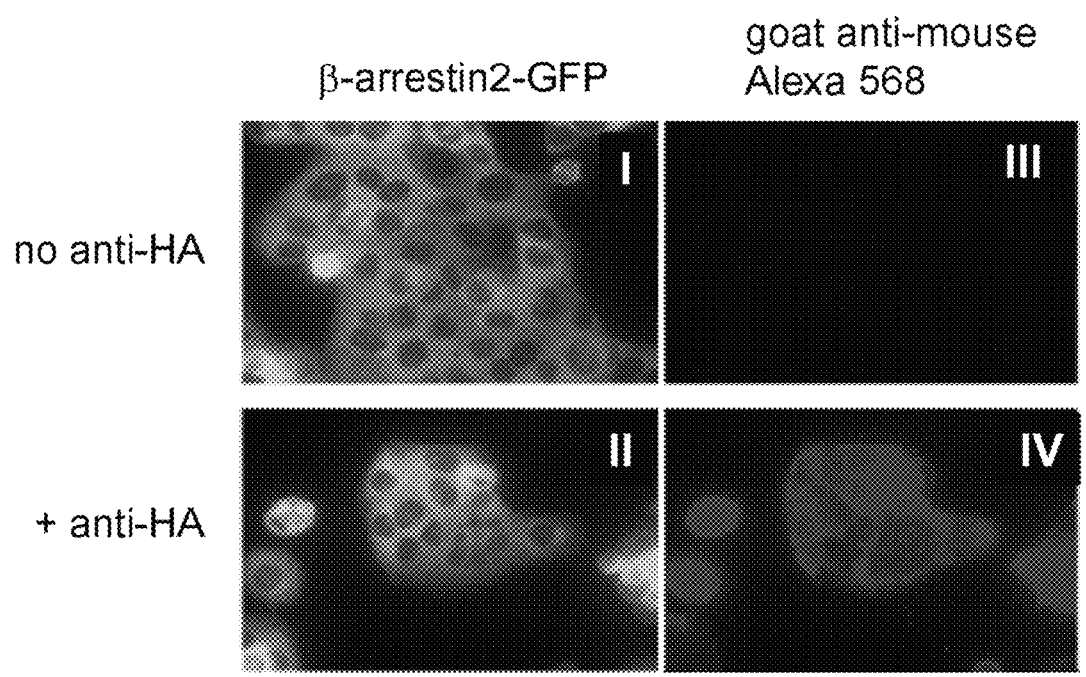
FIG. 2, comprising panels I-IV, shows fluorescence-derived images of UGPR35β cells. In panels I and III, the cells were not treated the anti-HA antibody. In panels II and IV, the cells were treated with the anti-HA antibody. In Panels I and II, fluorescence was excited with a fluorescein filter set (which would excite GFP fluorescence). In Panels III and IV, fluorescence was excited with a rhodamine set (which would excite Alexa568 fluorescence). Green fluorescence was registered as light gray areas in panels I and II, and red fluorescence was registered as dark-gray areas in panel IV.

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, protein chemistry and nucleic acid chemistry and hybridization are those well known and commonly employed in the art.

As used in the specification and the appended claims, the singular forms "a," "an" and "the" include plural referents unless the context clearly dictates otherwise.

The term "about" will be understood by persons of ordinary skill in the art and will vary to some extent on the context in which it is used.

As used herein, the terms "peptide," "polypeptide," or "protein" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. As used herein, the term "fragment," as applied to a protein or peptide, refers to a subsequence of a larger protein or peptide.

As used herein, amino acids are represented by the full name thereof, by the three-letter code, as well as the one-letter code corresponding thereto. The structure of amino acids and their abbreviations can be found in the chemical literature, such as in Stryer, 1988, "Biochemistry", 3rd Ed., W. H. Freeman & Co., NY, N.Y. Table 1 summarizes the natural α-amino acids and their corresponding representations.

TABLE 1

Natural α-amino acids and abbreviations.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "agonist" refers to a molecule that activates an intracellular response when it binds to the receptor. The term "agonist" also includes partial agonists, which are molecules that activate the intracellular response when they bind to the receptor to a lesser degree or extent than do full agonists.

As used herein, the term "antagonist" refers to a molecule that competitively binds to the receptor at the same site as an agonist but that does not activate an intracellular response, and can thereby inhibit an intracellular response elicited by the agonist. An antagonist does not diminish the baseline intracellular response in the absence of an agonist.

As used herein, the term "constitutively activated receptor" refers to a receptor subject to constitutive receptor activation. As used herein, the term "constitutive receptor activation" refers to the stabilization of a receptor in the active state by means other than binding of the receptor with its endogenous ligand or a chemical equivalent thereof.

As used herein, the term "GPR35" refers to a polypeptide with the amino acid sequence SEQ ID NO:1, the alternatively sliced form of GPR35a named GPR35b (SEQ ID NO:2), the sequence with the amino acid sequence SEQ ID NO:3 published by O'Dowd et al. (O'Dowd et al, 1998, Genomics 47:310-313) and encoded by GenBank Accession No. AF027957, the sequence in GenBank Accession No. AF158748 (nucleotides 60183-61112) (SEQ ID NO:4), or a variant or ortholog of these sequences that retains at least one function of a polypeptide with the amino acid sequence as referenced in SEQ ID NO:1, SEQ ID NO:2, SEQ ID NO:3, or SEQ ID NO:4. The sequence SEQ ID NO:1 encodes an alanine at position 174 and an arginine at position 294. The O'Dowd sequence (SEQ ID NO:3) encodes an arginine at position 174 and an arginine at position 294. The sequence SEQ ID NO:4 encodes an alanine at position 174 and a serine at position 294. Different sequences for GPR35 may be the result of allelic variations in the population. Thus, the definition of the term GPR35 as used herein includes both of these sequences as well as allelic variants.

As used herein, the terms "GPR35 receptor-positive cell" and "GPR35 receptor-expressing cell" refers to a cell that expresses on its surface GPR35 or allelic variants thereof.

As used herein, "isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein may exist in substantially purified form, or may exist in a non-native environment, such as a host cell for example.

As used herein, the term "pharmaceutically acceptable salt" refers to a salt of a compound, and hydrates or solvates thereof, that retains the desired biological activity of the compound and exhibits minimal undesired toxicological effects.

The counterion of a compound in a salt may be an anionic counterion or a cationic counterion. An anionic counter may be an anion or a molecule that easily converts into an anion by deprotonation. For example, both acetate ion and acetic acid are considered anionic counterions. A cationic counterion may be a cation or a molecule that easily converts into a cation by protonation. For example, both dimethylamine and dimethylammonium ion are considered cationic counterions.

In one embodiment, the pharmaceutically acceptable salt of the compound of Formula (I) is prepared with a cationic counterion selected from the group consisting of pyrantel and oxantel. In another embodiment, the pharmaceutically acceptable salt of the compound of Formula (I) is prepared using a counterion that has been approved by the FDA (U.S. Food and Drug Administration, Department of Health and Human Services) for pharmaceutical salt preparation. Particular FDA-approved salts can be conveniently divided between anionic and cationic counterions, as described in: "Approved Drug Products with Therapeutic Equivalence Evaluations" (1994), U.S. Department of Health and Human Services, Public Health Service, FDA, Center for Drug Evaluation and Research, Rockville, Md.; Bighley et al., "Salt Forms of Drugs and Absorption", Encyclopedia of Pharmaceutical Technology, Vol. 13, J. Swarbridk and J. Boylan, eds., Marcel Dekker, N.Y. (1996). The FDA-approved cationic counterions may be divided between non-metallic and metallic cationic counterions. The FDA-approved non-metallic cationic counterions include ammonium, benethamine [N-benzylphenethylamine], benzathine [N,N'-dibenzylethylenediamine], betaine [(carboxymethyl)trimethylammonium hydroxide], camitine, clemizole [1-p-chlorobenzyl-2-pyrrolidin-1'-yl-methylbenzimidazole], chlorcyclizine [1-(4-chlorobenzhydryl)-4-methylpiperazine], choline, dibenylamine, diethanolamine, diethylamine, diethylammonium, diolamine, eglumine [N-ethylglucamine], erbumine [t-butylamine], ethylenediamine, heptaminol[6-amino-2-methylheptan-2-ol], hydrabamine [N,N'-di(dihydroabietyl)ethylenediamine], hydroxyethylpyrrolidone, imadazole, meglumine [N-methylglucamine], olamine, piperazine, 4-phenylcyclohexylamine, procaine, pyridoxine, triethanolamine, and tromethamine [tris(hydroxymethyl)aminomethane]. The FDA-approved metallic cationic counterions include aluminum, bismuth, calcium, lithium, magnesium, neodymium, potassium, rubidium, sodium, strontium and zinc.

As used herein, the term "gastric inflammation" refers to inflammatory processes associated with the upper and lower gastrointestinal tract, and encompasses diseases such as celiac disease; ulcerative colitis; diverticulitis; gastroenteritis; inflammatory bowel disease (including Crohn's disease and ulcerative colitis); irritable bowel syndrome; pancreatitis; and peptic ulcer disease (including gastric ulcer, duodenal ulcer, oesophageal ulcer and Meckel's diverticulum ulcer).

"Biologically active," as used herein with respect to a compound, means that the compound has the ability to bind and act as an agonist to the GRP35 receptor.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

As applied to a GPR35 receptor in a cell, the term "effective amount" of a compound refers to an amount of the compound that increases the activity of the GPR35 receptor above its constitutive or baseline level.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, a "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

"Medical intervention", as used herein, means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

A "subject", as used therein, may be a human or non-human animal. Non-human animals include, for example, livestock and pets, such as ovine, bovine, porcine, canine, feline and murine mammals, as well as reptiles, birds and fish. Preferably, the subject is human.

As applied to treatment of a subject, the language "effective amount" or "therapeutically effective amount" refers to a nontoxic but sufficient amount of the composition used in the practice of the invention that is effective to provide antinociception, provide neuroprotection in stroke and ischemia, or treat gastric inflammation in the subject in need thereof. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, a species (which may be a neutral molecule, a salt, a cationic counterion or an anionic counterion) does not provide "therapeutically useful" treatment for a disease or disorder in a subject if the species is not effective in treating the disease or disorder at a dose level that does not cause unwanted side effects or toxic effects. The lack of therapeutically usefulness of the species may be determined by one of ordinary skill in the art using routine experimentation, by testing the species in an in vitro or in vivo assay that is thought to provide insight about the therapeutic effectiveness of a molecule.

A "pharmaceutically acceptable carrier" refers herein to a composition suitable for delivering an active pharmaceutical ingredient, such as a compound of Formula (I), to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed., Mack Publishing Co., 1985, Easton, Pa.), the disclosure of which is incorporated herein by reference.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., providing antinociception, providing neuroprotection in stroke and ischemia, or treating gastric inflammation in a subject in need thereof.

As used herein, the term "applicator" is used to identify any device including, but not limited to, a hypodermic syringe, a pipette, and the like, for administering the compounds and compositions used in the practice of the invention.

DETAILED DESCRIPTION OF THE INVENTION

The present invention is based on the unexpected discovery that certain 1,1'-binaphthyl and methylene-1,1'-binaphthyl compounds, or their pharmaceutically acceptable salts, are potent agonists of the orphan G protein-coupled receptor (GCPR) GPR35. Binding of these compounds to the GPR35 receptor causes activation of the receptor as judged by three distinct assays: receptor internalization, recruitment of β-ar-restin and activation of ERK1/2. These compounds may find use in providing antinociception, providing neuroprotection in case of stroke or ischemia, or treating gastric inflammation in a subject in need thereof. The subjects have advantageously been identified as being in need of one of the aforesaid treatments.

GPR35 Agonists

As one aspect of the invention, there is provided a compound according to Formula (I):

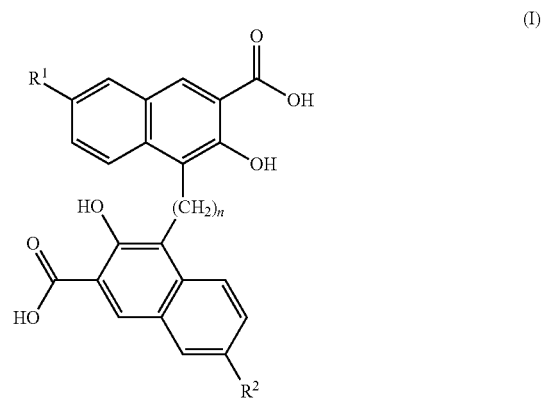

or a pharmaceutically acceptable salt thereof, wherein:
$R^1$ and $R^2$ are independently H, F, Cl, Br or I; and,
n is 0 or 1.

In a preferred embodiment, the compound of Formula (I) is 4,4'-methylenebis(3-hydroxy-2-naphthoic acid), or a pharmaceutically acceptable salt thereof. In another preferred embodiment, the compound of Formula (I) is oxantel pamoate. In yet another preferred embodiment, the compound of Formula (I) is pyrantel pamoate, or a pharmaceutically acceptable salt thereof. In yet another preferred embodiment, the compound of Formula (I) is 7,7'-dibromo-pamoic acid, or a pharmaceutically acceptable salt thereof. In yet another preferred embodiment, the compound of Formula (I) is 1,1'-binaphthyl-2,2'-diol-3,3'-dicarboxylic acid, or a pharmaceutically acceptable salt thereof.

Synthesis of the Compounds of Formula (I)

The compounds of Formula (I) may be obtained from commercial sources or prepared by methods known to the person skilled in the art of organic chemistry.

The compound of Formula (I), wherein n=1 and $R^1$ and $R^2$ are simultaneously H, is known as pamoic acid, embonic acid or 4,4'-methylene-bis(3-hydroxy-2-naphthoic acid). Pamoic acid may be prepared by condensing commercially available 3-hydroxy-2-naphthoic acid (Acros Organics, Fairlawn, N.J.) with formaldehyde or paraformaldehyde in the presence of sodium hydroxide (Strohbach, 1901, Chem. Ber. 34:4148; Hosaeus, 1892, Chem. Ber. 25:3215; Brass, 1928, Chem. Ber. 61:1001), as shown in Scheme I.

Scheme I.

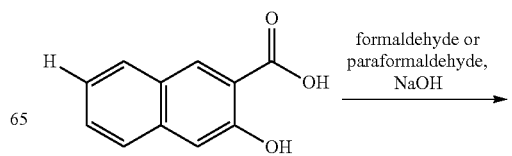

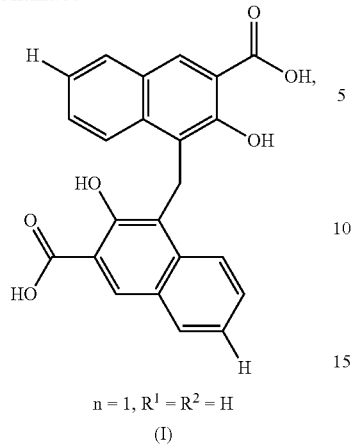

n = 1, R¹ = R² = H
(I)

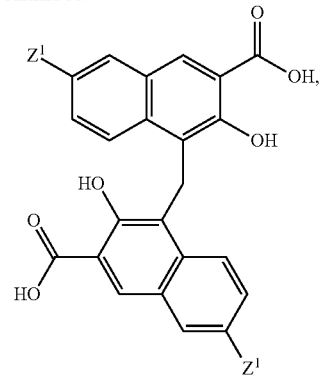

n = 1, R¹ = R² = Z¹
(I)

In a similar fashion, compounds of Formula (I), wherein n=1 and R¹ and R² are not simultaneously H, may be prepared by condensing 7-substituted-3-hydroxy-2-naphthoic acid with formaldehyde or paraformaldehyde in the presence of sodium hydroxide. 7-Substituted-3-hydroxy-naphthoic acid, wherein the 7-substitution is F, Cl, Br or I, may be prepared by regioselective halogenation of 3-hydroxy-naphthoic acid, using a procedure outlined by Ahn and coworkers (Ahn et al., 2002, Bioorg. Med. Chem Lett. 12:1941-1946).

A compound of Formula (I) wherein R¹ and R² are identical substituents may be prepared by reacting a 7-substituted-3-hydroxy-2-naphthoic acid (where the 7-substituent corresponds to R¹=R²) with formaldehyde or paraformaldehyde in the presence of sodium hydroxide, as shown in Scheme II.

Scheme II.

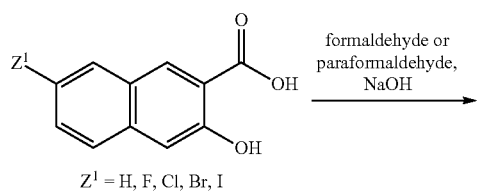

Z¹ = H, F, Cl, Br, I

If two different 7-substituted-3-hydroxy-2-naphthoic acids, wherein one of the acids has the group R¹ at the 7-position and the other acid has the group R² at the 7-position, are reacted with formaldehyde or paraformaldehyde in the presence of sodium hydroxide, a mixture of different compounds of Formula (I), wherein n=1, is formed, as shown in Scheme III. The ratio between the 3 possible products depends on the ratio of the two different 7-substituted-3-hydroxy-2-naphthoic acids in the reaction mixture, the reactivity of the two different 7-substituted-3-hydroxy-2-naphthoic acids and the overall conditions of the reaction. The products of this reaction may be separated using standard purification methods, such as chromatography or crystallization. This constitutes a non-limiting example of how a compound of Formula (I) with n=1 and different R¹ and R² groups may be prepared.

Scheme III.

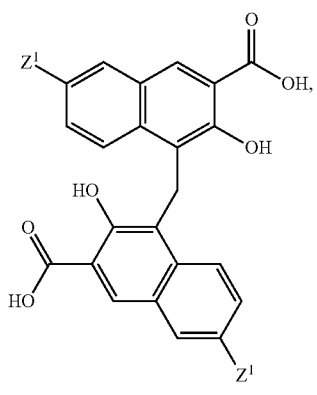

n = 1, R¹ = R² = Z¹
(I)

-continued

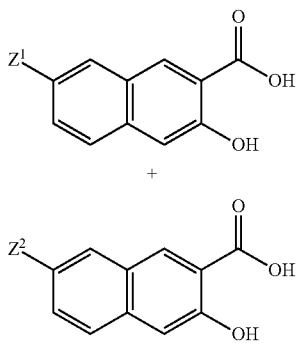

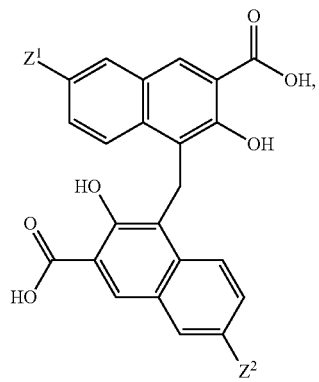

n = 1, R¹ =Z¹, R² = Z²
(I)

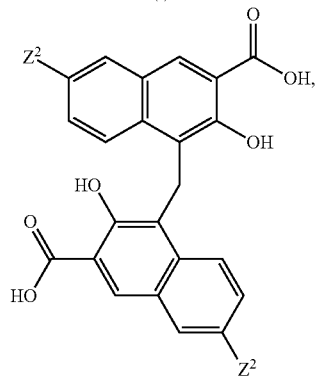

n = 1, R¹ = R² = Z²
(I)

The compound of Formula (I), wherein $R^1$ and $R^2$ are simultaneously H and n=0, is known as 2,2'-dihydroxy-3,3'-dicarboxy-1,1'-binaphthyl. It may be prepared by oxidative self-coupling of 3-hydroxy-2-naphthoic acid using metal-based oxidants (Scheme IV), such as the $V_2O_5$—$O_2$ system (Joseph et al., 2006, Catal. Comm 7:184-186), tridentate N-ketopinidene-based vanadyl dicarboxylate (Barhate & Chen, 2002, Org. Lett. 4 (15):2529-2532), alumina-supported copper(II) sulfate using dioxygen as oxidant (Sakamoto et al., 1994, J. Org. Chem. 59 (22):6859-6861), chiral copper(I)-bisoxazoline catalysts (Temma & Habaue, 2005, Tetrahedron Lett. 46 (34):5655-5657), ruthenium hydroxide on alumina in water (Kazuya et al., 2005, Symp. Organomet. Chem. Jpn. 52:402-403) and methyltrioxorhenium (Sharma et al., Tetrahedron Lett. 44 (13):2655-2656). In 2,2'-dihydroxy-3,3'-dicarboxy-1,1'-binaphthyl, intramolecular rotation is restricted around the single bond that connects the two naphthyl rings and the compound thus exists as a pair of optical isomers, which may be separated by methods such as chiral chromatography or seed-induced crystallization.

Scheme IV.

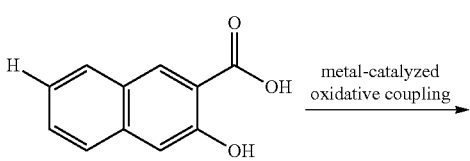

-continued

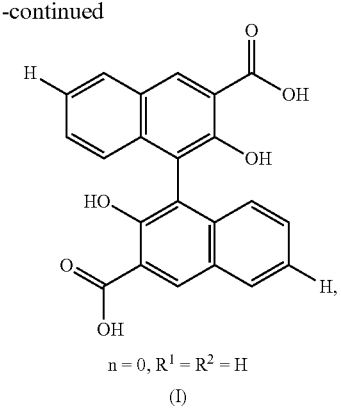

n = 0, R¹ = R² = H
(I)

Compounds of Formula (I), wherein n=0 and $R^1$ and $R^2$ are not simultaneously H, may be prepared by oxidative coupling of 7-substituted-3-hydroxy-2-naphthoic acid with metal oxidants, as described above. 7-Substituted-3-hydroxy-naphthoic acid, wherein the 7-substitution is F, Cl, Br or I, may be prepared by regioselective halogenation of 3-hydroxy-2-naphthoic acid, as described above.

A compound of Formula (I), wherein n=0 and $R^1$ and $R^2$ are identical substituents, may be prepared by oxidative coupling of a 7-substituted-3-hydroxy-2-naphthoic acid where the 7-substituent corresponds to $R^1=R^2$, as shown in Scheme V.

Scheme V.

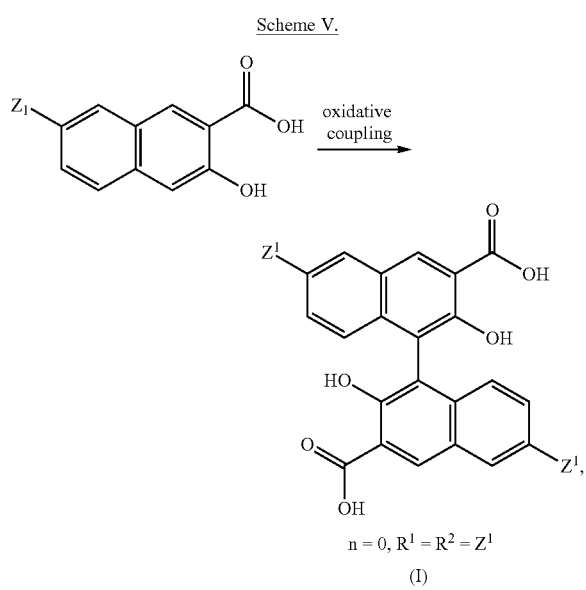

If two different 7-substituted-3-hydroxy-2-naphthoic acids, wherein one of the acids has the group $R^1$ at the 7-position and the other acid has the group $R^2$ at the 7-position, are oxidatively coupled, mixture of different compounds of Formula (I), wherein n=0, is formed, as shown in Scheme VI. The ratio between the 3 possible products depends on the ratio of the two different 7-substituted-3-hydroxy-2-naphthoic acids in the system, the reactivity of the two different 7-substituted-3-hydroxy-2-naphthoic acids and the overall conditions of the reaction. The products of this reaction may be separated using standard purification methods, such as chromatography or crystallization. For these 2,2'-dihydroxy-3,3'-dicarboxy-1,1'-binaphthyl compounds, rotation is restricted around the single bond that connects the two naphthyl rings and each compound thus exists as a pair of optical isomers, which may be separated by methods such as chiral chromatography or seed-induced crystallization. This constitutes a non-limiting example of how a compound of Formula (I) with n=0 and different $R^1$ and $R^2$ groups may be prepared.

Scheme VI.

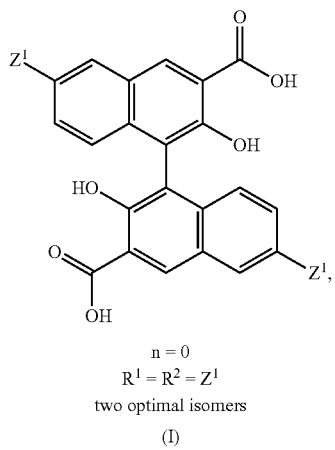

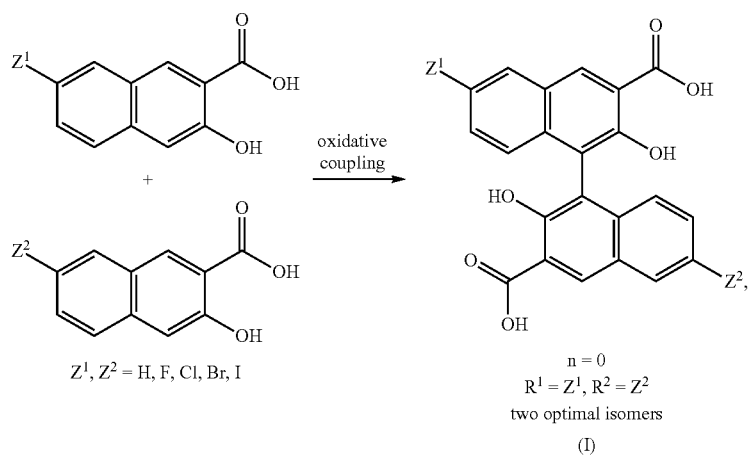

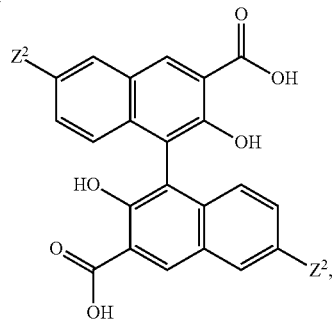

n = 0
R¹ = R² = Z²
two optimal isomers (I)

Salts of the Compounds of Formula (I)

The compounds of Formula (I) may form salts with acids or bases, and such salts are included in the present invention. The term "salts" embraces addition salts of free acids or free bases that are compounds of Formula (I). Preferred salts are formed from cationic and anionic counterions that have been approved by the FDA for pharmaceutical applications, as well as cationic counterions selected from the group consisting of pyrantel and oxantel. Pharmaceutically unacceptable salts may nonetheless possess properties such as high crystallinity, which have utility in the practice of the present invention, such as for example utility in process of synthesis, purification or formulation of compounds of Formula (I).

Pharmaceutically acceptable base addition salts of compounds of Formula (I) include, for example, metallic salts and non-metallic salts. Metallic cationic counterions include alkali metal, alkaline earth metal and transition metal ions such as, for example, aluminum, bismuth, calcium, lithium, magnesium, neodymium, potassium, rubidium, sodium, strontium and zinc. Non-metallic cationic counterions include organic basic amines such as, for example, ammonium, benethamine [N-benzylphenethylamine], benzathine [N,N'-dibenzylethylenediamine], betaine [(carboxymethyl) trimethylammonium hydroxide], carnitine, clemizole [1-p-chlorobenzyl-2-pyrrolidin-1'-ylmethylbenzimidazole], chlorcyclizine [1-(4-chlorobenzhydryl)-4-methylpiperazine], choline, dibenylamine, diethanolamine, diethylamine, diethylammonium, diolamine, eglumine [N-ethylglucamine], erbumine [t-butylamine], ethylenediamine, heptaminol[6-amino-2-methylheptan-2-ol], hydrabamine [N,N'-di(dihydroabietyl)ethylenediamine], hydroxyethylpyrrolidone, imadazole, meglumine [N-methylglucamine], olamine, piperazine, 4-phenylcyclohexylamine, procaine, pyridoxine, triethanolamine, and tromethamine [tris(hydroxymethyl)aminomethane]. Other examples of pharmaceutically acceptable cationic counterparts are oxantel and pyrantel. Examples of pharmaceutically unacceptable base addition salts include lithium salts. All of these salts may be prepared from the corresponding compound by reacting, for example, the appropriate acid or base with the compound.

Activity of the Compounds of Formula (I)

In an aspect, a compound of Formula (I) has agonistic activity against GPR35. As used herein, "agonistic activity" means that a compound is able to activate the receptor and result in a biological response that is enhanced over the baseline response of the unbound receptor.

The agonistic activity of a compound against GPR35 may be assayed using one or more of three distinct in vitro assays: intracellular β-arrestin redistribution; ligand-induced receptor internalization; and ERK1/2 activation.

Qualitative Evaluation of Compounds of Formula (I):

(i) Intracellular β-Arrestin Redistribution

Compounds may be assayed for agonistic activity against GPR35 using the cellular assay set forth in Example 1. This cellular assay utilizes the intracellular β-arrestin protein as a reporter of receptor activity. Ligand-activated GPCR desensitization requires receptor phosphorylation by a G protein-coupled receptor kinase (GRK) and phosphorylation-mediated receptor binding of an intracellular β-arrestin protein (Barak et al., 1997, J. Biol. Chem. 272 (44): 27497-27500; Palczewski & Benovic, 1991, Trends Biochem. Sci. 16 (10): 387-391). High-content cell imaging employing chimeric fusions between β-arrestins and green fluorescent proteins (GFP) provides a reliable means to recognize the activation states of GPCRs (Barak et al., 1997, Mol Pharmacol 51 (2): 177-184). Upon agonist-mediated GPCR activation, β-arrestins rapidly redistribute en masse to ligand-activated plasma membrane receptors (on the other hand, β-arrestins remain in the cytosol upon antagonist binding to the receptor). Activated GPCR/β-arrestin complexes will concentrate in clathrin-coated pits and/or internal vesicles where most GPCRs normally undergo internalization. At this juncture, the β-arrestin either (i) dissociates and returns to the cytoplasm, or (ii) further redistributes with the receptor into an intracellular endosomal vesicle, depending on the receptor type. It is the agonist-induced redistribution of β-arrestin-GFP into progressively smaller compartments (cytosolic compartment>plasma membrane>coated pit>endosomal compartment) that enables imaging of receptor activation.

Quantitative Evaluation of Compounds of Formula (I):

(i) Intracellular β-Arrestin Redistribution

The cellular assay described above may be used to determine the agonist dissociation constant $K_{Dh}$ for a compound of interest. In a non-limiting example, the cell line permanently expressing the β-arrestin-GFP construct is contacted with various concentrations of the compound of interest, and the cells are then analyzed for fluorescence. β-arrestin-GFP redistribution, which is detected as a fluorescence signal, is analyzed using a theoretical model summarized in the equation:

$$R_{arr}/B_T = A/(1+\tau \cdot K_{Dh}/[\text{agonist}])$$

in which the fraction of agonist-translocated β-arrestin $R_{arr}/B_T$ follows a sigmoidal dose response with respect to the agonist dissociation constant $K_{Db}$, wherein $B_T$ is total cell β-arrestin and τ is a number on the order of one or less. A complete theoretical discussion is provided by Barak and coworkers (Barak et al., 2003, Assay Drug Dev. Technol 1 (3): 409-424).

(ii) Ligand-Induced Receptor Internalization

As described in Example 3, binding of an agonist to GPR35 was found to induce translocation of the receptor from plasma membrane to form clusters in the cytosol. As a result, the level of GPR35 located on the plasma membrane decreases as higher concentrations of agonists are added to the system. Loss of cell surface receptor may be evaluated by methods such as On-Cell Western analysis of the cells under treatment.

In a non-limiting example, a cell line that expresses N-terminal triple HA-tagged GPR35 receptor is used. After contacting the cells with a candidate GPR35 agonist and incubating the system for a set period of time, the cells are incubated with an anti-HA mouse antibody, followed by incubation with a fluorophore-labeled anti-mouse antibody. The resulting observed fluorescence is then used to assess the level of GPR35 receptor on the cell surface.

(iii) ERK1/2 Activation

As described in Example 4, binding of an agonist to GPR35 was found to induce time-dependent phosphorylation of ERK1/2. This property allows for the evaluation of a compound as a potential agonist of GPR35.

In a non-limiting example, the cells of interest are incubated with a compound for a defined period of time, and then lysed in the presence of a protease inhibitor cocktail. The supernatant, containing the cytosolic fraction, is then separated on a SDS-PAGE gel, followed by immunoblotting with antibodies against phosphorylated ERK1 and/or ERK2. In this procedure, the level of phosphorylated ERK detected depends on the duration of incubation of the cell with the compound, since phosphorylated ERK1/2 is initially formed and then consumed by cellular dephosphorylating processes. One skilled in the art should be able to determine the optimal incubation time for this assay using routine experimentation. For example, one skilled in the art may set up parallel experiments with varying incubation times and assess the resulting levels of detected phosphorylated ERK as a function of the incubation time.

Methods of Treatment Using Compounds of Formula I

The compounds of Formula (I) are useful as GPR35 agonists. They bind to GPR35 and agonize GPR35-mediated activity, and may thus be used for the treatment of diseases and conditions that benefit from a GPR35-mediated upregulation in cell signaling and growth. Accordingly, as non-limiting examples, compounds of Formula (I) may be used to provide antinociception, provide neuroprotection in case of stroke or ischemia, or treat gastric inflammation. The aforementioned conditions are related to, at least in part, to low or insufficient activity of the GPR35 receptor in a cell or tissue.

Therefore, an individual who is in need of treatment according to the instant invention may be an individual who suffers from acute or chronic high levels of nociception, requires neuroprotection in the event of stroke or ischemia, or suffers from gastric inflammation, among other disorders.

In one aspect of the present invention, the inventors have surprisingly discovered that the compounds for the invention may be used to promote antinociception. The term "nociception" is defined as "the neural processes of encoding and processing noxious stimuli" (Loeser & Treede, 2008, Pain 137 (3):473-7). It corresponds to the activity produced in the peripheral and central nervous system by stimuli that have the potential to damage tissue. Nociception, the unconscious activity induced by a harmful stimulus in sense receptors, peripheral nerves, spinal column and brain, should not be confused with physical pain, which is a conscious experience. Nociception or noxious stimuli usually cause pain, but not always, and sometimes pain occurs without them.

Nociception is initiated by pain receptors (nociceptors) found in the skin and on internal surfaces such as the periosteum or joint surfaces. The nociceptors can detect mechanical, thermal or chemical changes, above a set threshold. The concentration of nociceptors varies throughout the body, and these receptors are mostly found in the skin but also in deep internal surfaces. Once stimulated, a nociceptor transmits a signal along the spinal cord, to the brain. Nociception triggers a variety of autonomic responses and may also result in the experience of pain in the subject. In some conditions, excitation of pain fibers becomes greater as the pain stimulus continues, leading to a condition called hyperalgesia.

Compounds that have the effect of reducing sensitivity to painful stimuli are commonly referred to as antinociceptors, finding use in the treatment of a subject with acute or chronic high levels of nociception. Among the validated models for antinociception is the chemically induced writhing test (Svendesen & Hau, "Handbook of Laboratory Animal Science", Vol. II, CRC Press, Boca Raton, Fla., 1994). In this test, the intraperitoneal injection of an irritant induces a syndrome called "writhing", which consists of contractions of the abdomen, twisting and turning of the trunk, and extension of the hind limbs. Several compounds have been shown to elicit this syndrome, such as phenylquinone, acetic acid, bradykinin and acetylcholine. In recent years acetic acid (Koster et al., 1959, Fed. Proc. 18:412) and phenylquinone have been more frequently used. Administration of relatively small doses of non-narcotic drugs, especially the non-steroid anti-inflammatory drugs, abolishes the writhing syndrome in a dose-dependent manner. The test is commonly employed as a screening method because of it simplicity and sensitivity. The main disadvantage of this method is its lack of specificity, as many drugs without certain analgesic effects in humans can effectively inhibit the writhing effect. In addition, there may be a large variation in the response among mouse strains.

The mechanism of the writhing syndrome is unknown, but many mediators have been proposed. No significant differences were detected in histamine, serotonin, or prostaglandin content of peritoneal fluid from writhing (using phenylquinone as an irritant) and control mice, while other reports indicate involvement of the prostaglandin system in writhing induced by at least some irritants. It has been claimed that different irritants may be considered as models of different pain reactions, distinguishing between inflammatory and non-inflammatory pain. The writhing test is most widely applied in mice, but it has been used in rats as well. The test is simple to perform, is sensitive and widely used.

One version of the acetic acid writhing test was published by Porreca and co-workers (J. Pharmacol. Exp. Ther., 1987, 240(3):890-894). In this model, mice are treated with the compound of interest and then challenged with i.p. treatment of acetic acid (generally 0.6% or higher). Writhing behavior of the animals, as a function of the dose of compound of interest, is monitored over time. As shown in Example 5, a compound of Formula (I) demonstrated dose-dependent antinociceptive effect in mice. Administration of a therapeutically effective amount of a compound of Formula (I) to a subject with excessive or uncontrolled nociception thus promotes the desired antinociception.

In one embodiment, the invention includes a method of promoting antinociception in a subject in need thereof. The method comprises administering a therapeutically effective amount of a compound of Formula (I) or a therapeutically acceptable salt thereof, or a therapeutically effective amount of a pharmaceutical composition comprising a compound of Formula (I) or a therapeutically acceptable salt thereof, as described herein, to an individual in need of such treatment or prophylaxis. In one aspect, administration of a compound of Formula (I) will provide relief to the subject, by agonizing the GPR35 receptor and regulating excessive or uncontrolled nociception.

In another aspect of the invention, the inventors have surprisingly discovered that the compounds of Formula (I) may be used to provide neuroprotection in case of stroke or ischemia. The term "neuroprotection" refers to mechanisms within the nervous system that protect neurons from injury, apoptosis or degeneration, for example following acute disorders (e.g. stroke or nervous system injury/trauma) or as a result of chronic neurodegenerative diseases (e.g. Parkinson's, Alzheimer's, multiple sclerosis). The goal of neuroprotection is to limit neuronal dysfunction/death after central nervous system injury and attempt to maintain the highest possible integrity of cellular interactions in the brain resulting in an undisturbed neural function.

The term "ischemia" refers to a restriction in blood supply to a tissue in the body, generally due to factors in the blood vessels, with resultant damage or dysfunction of tissue. Ischemia causes a shortage of oxygen, glucose and other blood-borne fuels to the tissue, and ultimately causes severe damage because of the build-up of metabolic wastes in the tissue. Ischemia of heart muscle produces angina pectoris. Ischemia leads to excessive activation of excitatory amino acid receptors, accumulation of intracellular calcium, and release of other toxic products that cause cellular injury. By preventing excitatory neurotransmitter release, neuroprotective agents may reduce deleterious effects of ischemia on cells. Restoration of blood flow after a period of ischemia may actually be more damaging than the ischemia. Reintroduction of oxygen causes a greater production of damaging free radicals, resulting in reperfusion injury. With reperfusion injury, necrosis may be greatly accelerated.

Stroke is the third leading cause of death in the United States and the most common cause of adult disability. An ischemic stroke occurs when a cerebral vessel occludes, obstructing blood flow to a portion of the brain. The only currently approved medical stroke therapy, tissue plasminogen activator (tPA), is a thrombolytic agent that targets the thrombus within the blood vessel. Neuroprotective agents, an alternative approach to stroke treatment, have generated great interest, since they attempt to save ischemic neurons in the brain from irreversible injury. Studies in animals indicate a period of at least 4 hours after onset of complete ischemia in which many potentially viable neurons exist in the ischemic penumbra. In humans, the ischemia may be less complete, and the time window may be longer, but human subjects also tend to be older with co-morbidities that may limit benefit. Neuroprotective agents may limit acute injury to neurons in the penumbra region or rim of the infarct after ischemia. Neurons in the penumbra are less likely to suffer irreversible injury at early time points than are neurons in the infarct core. Many of these agents modulate neuronal receptors to reduce release of excitatory neurotransmitters, which contribute to early neuronal injury. Neuroprotective agents may also prevent potentially detrimental events associated with return of blood flow. Although return of blood flow to the brain is generally associated with improved outcome, reperfusion may contribute to additional brain injury. Returning blood contains leukocytes that may occlude small vessels and release toxic products.

Several animal-based models for stroke have been proposed and validated, such as the artery occlusion and reperfusion model in male mice described by Zhang and coworkers (Microvasc. Res., 2009, 78(1):86-94). In this model, the animals are submitted to middle cerebral artery occlusion for a period of 60 minutes and then reperfusion is allowed. Cerebral infarction volume is measured by analyzing sections of the animal brain stained with triphenyltetrazolium chloride. Triphenyltetrazolium chloride is believed to be reduced to red formazan by mitochondrial enzymes, specifically succinate dehydrogenase (Lippold, 1982, Histochemistry 76:381-405). On immediate TTC staining after the elective or natural death of animals, the normal tissue stains deep red and infarcted tissue with loss of mitochondrial enzyme activity does not stain and appears white (Liszczak et al., 1984, Acta Neurophatol. (Berl) 65:150-157.; Bose et al., 1984, Brain Res. 311:385-391; Bederson et al., 1986, Stroke 17:1304-1308; Park et al., 1988, Neuropathol. Appl. Neurobiol. 14:289-298). The border between stained and unstained tissues is well demarcated and identified easily by visual inspection (Bederson et al., 1986, Stroke 17:1304-1308; Isayama et al., 1991, Stroke 22:1394-1398). Many studies demonstrate that TTC staining can rapidly and accurately detect brain infarction from 12 hours to 3 days after the onset of ischemia and is a reliable indicator of infarction extent (Bederson et al., 1986, Stroke 17:1304-1308; Taylor et al., 1987, Neurology 37:82; Lin et al., 1993, Stroke 24:117-121). Therefore, TTC staining is extensively used in animal stroke experiments for quantitatively delineating the infarct volume (Memezawa et al., 1992, Exp. Brain Res. 89:67-78.; Hasegawa et al., 1995, J. Cereb. Blood Flow Metab. 15:179-187; Kuge et al., 1995, Stroke 26:1655-1658; Fuhai et al., 1997, J. Cereb. Blood Flow Metab. 17:1132-1135).

As shown in Example 6, a compound of Formula (I) demonstrated neuroprotection in an animal model of stroke. Administration of a therapeutically effective amount of a compound of Formula (I) to a subject that has suffered a stroke or general ischemia may thus provide desired neuroprotection.

In one embodiment, the invention includes a method of providing neuroprotection in case of stroke or ischemia to a subject in need thereof. The method comprises administering a therapeutically effective amount of a compound of Formula (I) or a therapeutically acceptable salt thereof, or a therapeutically effective amount of a pharmaceutical composition comprising a compound of Formula (I) or a therapeutically acceptable salt thereof, as described herein, to an individual in need to such treatment or prophylaxis. In one aspect, administration of a compound of Formula (I) will benefit the subject that requires neuroprotection in case of stroke or general ischemia because the compound agonizes the GPR35 receptor.

In yet another aspect of the invention, the inventors have surprisingly discovered that compounds of Formula (I) may be used to treat gastric inflammation. The term "gastric inflammation" is a generic term used to describe inflammatory processes associated with the upper and lower gastrointestinal tract, and encompasses diseases such as celiac disease; ulcerative colitis; diverticulitis; gastroenteritis; inflammatory bowel disease (including Crohn's disease and ulcerative colitis); irritable bowel syndrome; pancreatitis;

and peptic ulcer disease (including gastric ulcer, duodenal ulcer, oesophageal ulcer and Meckel's diverticulum ulcer). Expression analysis by quantitative reverse transcriptase-mediated PCR revealed that both human GPR35 and mouse GPR35 were predominantly expressed in immune and gastrointestinal tissues, with limited expression in other tissues (Wang et al., J. Biol. Chem. 281 (31):22021-22028). In humans, GPR35 messenger RNA was mainly detected in the peripheral leukocytes, spleen, small intestine, colon, and stomach. GPR35 is enriched in the intestinal crypts of Lieberkühn, which are rich in actively proliferating stem cells and progenitor cells crucial for the self-renewal of gastrointestinal epithelium (Hauck et al., 2005, Birth Defects Res. C. Embryo Today 75:58-71). Interestingly, kynurenic acid, a proposed ligand for GPR35, was shown to exist in elevated plasma levels in subjects with inflammatory bowel diseases (Forrest et al., 2003, Adv. Exp. Med. Biol. 527:395-400; Forrest et al., 2002, J. Biomed. Sci. 9:436-442). It is thus likely that GPR35 has a role in inflammatory bowel diseases and other gastrointestinal disorders. Therefore, an agonist of this receptor may find use as a therapeutic agent for the treatment of gastric inflammation.

In one embodiment, the invention includes a method of treating gastric inflammation in a subject in need of such treatment. The method comprises administering a therapeutically effective amount of a compound of Formula (I) or a therapeutically acceptable salt thereof, or a therapeutically effective amount of a pharmaceutical composition comprising a compound of Formula (I) or a therapeutically acceptable salt thereof, as described herein, to an individual in need to such treatment or prophylaxis. In one aspect, administration of a compound of Formula (I) will benefit the subject that requires treatment of gastric inflammation because the compound agonizes the GPR35 receptor.

Pharmaceutical Compositions

The formulations of the pharmaceutical compositions described herein may be prepared by any method known or hereafter developed in the art of pharmacology. In general, such preparatory methods include the step of bringing the active ingredient or agent (compound of Formula (I) or a therapeutically acceptable salt thereof) into association with a carrier or one or more other accessory ingredients, and then, if necessary or desirable, shaping or packaging the product into a desired single- or multi-dose unit.

The active agent may be administered in the form of a pharmaceutical composition, in combination with a pharmaceutically acceptable carrier. The active agent in such formulations may comprise from 0.1 to 99.99 weight percent. "Pharmaceutically acceptable carrier" means any carrier, diluent or excipient that is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations (Alphonso Gennaro, ed., Remington's Pharmaceutical Sciences, 18th Edition (1990), Mack Publishing Co., Easton, Pa.). Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl-paraben, propyl-paraben, and chlorbutanol. The composition for parenteral administration may take the form of an aqueous or non-aqueous solution, dispersion, suspension or emulsion. Such formulations may be prepared, packaged, or sold in a form suitable for bolus administration or for continuous administration. Injectable formulations may be prepared, packaged, or sold in unit dosage form, such as in ampules or in multidose containers containing a preservative. In one embodiment of a formulation for parenteral administration, the active ingredient is provided in dry (e.g. powder or granular) form for reconstitution with a suitable vehicle (e.g. sterile pyrogen free water) prior to parenteral administration of the reconstituted composition.

A typical pharmaceutical composition for intravenous administration would be about 0.1 to 100 mg per subject per day. Dosages from 0.1 up to about 300 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., 1980, Mack Publishing Company, Easton, Pa.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods. Other formulations suitable for oral administration include, but are not limited to, a powdered or granular formulation, an aqueous or oily suspension, an aqueous or oily solution, or an emulsion. As used herein, an "oily" liquid comprises a carbon-containing liquid molecule that exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Powdered and granular formulations of a pharmaceutical preparation used in the practice of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition used in the practice of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

The compositions are preferably formulated in a unit dosage form, each dosage containing from about 1 to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein, using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a subject. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a subject, preferably a mammal, having a body temperature high enough to induce gel formation of the sol-gel matrix, thereby releasing the active ingredient into the subject.

Administration of Compositions of the Invention

In general, the schedule or timing of administration of a composition of the invention is according to the accepted practice for the procedure being performed. Multiple GPR35 agonists, including one or more GPR35 agonists according to Formula (I) and optionally one or more other GPR35 agonists, may be administered. All of the various compounds to be administered need not be administered together in a single formulation. The different compounds may be administered in separate formulations. For example, if three different compounds are to be administered, the three different compounds may be delivered in three separate formulations. In addition, each compound may be delivered at the same time, or the compounds may be delivered consecutively with respect to one another. Thus, the mixture of the compounds may be administered in a single formulation, or in multiple formulations comprising one or more compounds.

The compound and pharmaceutical composition comprising the compound may be administered by any method designed to allow compounds to have a physiological effect. Pharmaceutical compositions that are useful in the methods used in the practice of the invention may be prepared, packaged, or sold in formulations suitable for intravenous, oral, rectal, subcutaneous, intranasal, intracisternal, intravaginal, intraperitoneal or local, or another route of administration. Other contemplated formulations include projected nanoparticles, liposomal preparations, resealed erythrocytes containing the active ingredient, and immunologically-based formulations. Single or multiple administrations of the compositions may be administered depending on the dosage and frequency as required and tolerated by the subject. In any event, the administration regime should provide a sufficient quantity of the composition of this invention to effectively treat the subject.

Administration may occur enterally or parenterally; for example intravenously, orally, rectally, intracisternally, intravaginally, intraperitoneally, intranasally, subcutaneously or locally.

One preferred mode of administration is parenteral administration. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like.

Particularly preferred parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intrasternal injection, kidney dialytic infusion techniques, intraperitoneal injection, and direct application to the target area, for example by a catheter or other placement device.

Another preferred mode of administration is oral administration. A formulation of a pharmaceutical composition used in the practice of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient.

Controlled- or sustained-release formulations of a pharmaceutical composition used in the practice of the invention may be made using conventional technology. The pharmaceutical compositions of the present invention developed for slow or controlled release of the active ingredient may include hydropropylmethyl cellulose in varying proportions to provide the desired release profile, other polymer matrices, gels, permeable membranes, osmotic systems, multi-layer coatings, microparticles, liposomes and/or microspheres.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a subject. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a subject, preferably a mammal, having a body temperature high enough to induce gel formation of the sol-gel matrix, thereby releasing the active ingredient into the subject.

Another preferred mode of administration is pulmonary administration. A pharmaceutical composition of the invention may be prepared, packaged or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container, such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent, such as sugar, and are conveniently provided in a unit dose form.

Another preferred mode of administration is intranasal delivery. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nasal passages. Formulations suitable for nasal administration may, for example, comprise from about as little as 0.1% (w/w) and as much as 100% (w/w) of the active ingredient, and may further comprise one or more of the additional ingredients described herein.

The pharmaceutical compositions of the invention may be dispensed to the subject under medical intervention with the help of an applicator. The applicator to be used may depend on the specific medical condition being treated, amount and physical status of the pharmaceutical composition, and choice of those skilled in the art.

Typically it is contemplated that treatment would be given at least once per day, typically once, twice, three times or four times per day with the doses given at equal intervals throughout the day and night in order to maintain a constant presence of the drug in order to induce sufficient agonistic activity in GPR35. However, the skilled artisan will be aware that a treatment schedule may be optimized for any given subject, and that administration of compound may occur less frequently than once per day.

One or more GPR35 agonists may be administered simultaneously, by the same or different routes, or at different times during treatment. The compounds may also be prescribed to be taken in combination with other drugs used to provide antinociception, provide neuroprotection in case of stroke or ischemia, or treat gastric inflammation. When used in such combinations, GPR35 agonists of Formula (I) and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on the response of the subject/patient.

The specific dose of an active agent to obtain therapeutic benefit in the treatment of a disease will, of course, be determined by the particular circumstances of the individual subject including the size, weight, age and sex of the subject, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The pharmaceutical composition of the invention may be provided to the subject or the medical professional in charge of dispensing the composition to the subject, along with instructional material. The instructional material includes a publication, a recording, a diagram, or any other medium of expression, which can be used to communicate the usefulness of the composition and/or compound used in the practice of the invention in a kit. The instructional material of the kit may, for example, be affixed to a container that contains the compound and/or composition used in the practice of the invention or may be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there may be employed conventional clinical, chemical, cellular, histochemical, biochemical, molecular biology, microbiology and recombinant DNA techniques that are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is described hereafter with reference to the following examples. The examples are provided for the purpose of illustration only and the invention should in no way be construed as being limited to these examples, but rather should be construed to encompass any and all variations that become evident as a result of the teaching provided herein.

Materials

Pamoic acid was obtained from Sigma Aldrich Chemicals, St. Louis, Mo., USA. Zeocin®, a copper-chelated glycopeptide antibiotic produced by *Streptomyces* CL990, was obtained from InvivoGen (San Diego, Calif.). G418® or Geneticin® (Gibco BRL Life Technologies, Inc) was obtained from Invitrogen (Carlsbad, Calif.).

Methods

Plasmid Construction and Cell Culture

GFP conjugated to carboxy terminus of β-arrestin2 (βarr2-GFP) was described by Barak and coworkers (J. Biol.

Chem. 1997, 272(44):27497-27500). An U2OS osteosarcoma double stable cell line expressing HA-GPR35a/βarr2-GFP in the plasmid pcDNA3.1zeo+ was engineered using conditions previously described (Barak et al., 1997, J. Biol. Chem. 272 (44):27497-27500; Oakley et al., 1999, J. Biol. Chem. 274 (45):32248-32257; Oakley et al., 2001, J. Biol. Chem. 276 (22):19452-19460). This cell line is herein referred to as UGPR35β. Selected cells were maintained at 200 µg/ml G418® and 100 µg/ml Zeocin® at 37° C. and 5% $CO_2$.

On-Cell Western Assay

The previously described U2OS cells expressing HA-GPR35a/βarr2-GFP (also known as UGPR35β cells) were seeded and grown until confluence on the bottoms of a 96-well plate. Cells were incubated with monoclonal mouse anti-HA antibody (Covance, Princeton, N.J., USA) at 1:100 dilution for 45 minutes. Cells were washed once with Hanks' balanced salt solution (HBSS, Cellgro, Mediatech, Inc, Manassas, Va., USA) prior to appropriate drug treatment and then fixed with 4% formaldehyde for 20 minutes at room temperature. This step was followed by three washes with PBS for 5 minutes each. The cells were then treated with LI-COR Odyssey® blocking buffer (LI-COR, Lincoln, Nebr., USA) for 45 minutes at room temperature.

The secondary antibody (IRDye 800 conjugated anti-mouse IgG, Rockland, Gilbertsville, Pa.; 1:1000 in LI-COR Odyssey® blocking buffer) was then added to the treated cells and incubated for 1 hour at room temperature protected from light. The cells were then washed five times in TBST (137 mM NaCl, 10 mM Tris with 0.05% Tween-20) and scanned on the LI-COR Odyssey® Infrared imager (Lincoln, Nebr., USA). Integrated intensities were captured (169 µM resolution, 4 focus offset, 4.5-6 intensity setting at 700 and 800 channels) and analyzed using Excel and Prism 4.0 software.

β-Arrestin Trafficking

U2OS cells expressing HA-GPR35a/βarr2-GFP (also known as UGPR35β cells) were plated in a 24-well plate onto coverslips that were coated with poly-D-lysine (0.02 mg/ml; Sigma-Aldrich, St. Louis, Mo., USA) for 1 hour. Cells were maintained at 37° C., 5% $CO_2$ until ready for experiment (90% confluent). Cells were washed once with Hanks' balanced salt solution (HBSS, Cellgro, Mediatech, Inc, Manassas, Va., USA) comprising $CaCl_2$ 0.14 g/L, KCl 0.4 g/L, $KH_2PO_4$ 0.06 g/L, $MgSO_4$ 0.097 g/L, NaCl 8 g/L, $Na_2HPO_4$ 0.047 g/L, $NaHCO_3$ 0.35 g/L, and D-glucose 1.0 g/L. For receptor activation, agonist-evoked redistribution of βarr2-GFP was measured by applying the drug for 40 minutes. For measuring the effects of antagonist, agonist and antagonist were co-applied.

Cells were then fixed with 4% paraformaldehyde for 20 minutes at room temperature, followed by three washes with HBSS. Coverslips were mounted on slides in SlowFade® Gold mounting media (Invitrogen, Carlsbad, Calif.) and, if present, cytosolic βarr2-GFP aggregates were visualized with a fluorescence microscope (Nikon E800) at 40× magnification and 488 nm excitation for GFP. βarr2-GFP aggregates were quantified by using ImageJ software (Collins, 2007, BioTechniques 43 (1 Suppl):25-30) with an automated macro.

Receptor Internalization

Cells grown on coverslips were incubated over ice for 40 minutes with a 1:500 dilution of mouse monoclonal anti-HA antibody in blocking buffer (3% BSA in PBS), followed by three consecutive washes with PBS. The cells were then incubated for 40 minutes with 1:1500 dilution of Alexa Fluor 568 goat anti-mouse secondary antibody. Antibody-labeled cells were treated with agonist alone or in combination with antagonist for 40 minutes at 37° C., and the cells were then imaged.

Western Blot Analysis for ERK Activity (Phospho-ERK Assay)

UGPR35β cells were grown to sub-confluence in 60 mm plates and serum-starved overnight prior to ERK assay. Following treatment with compound, the cells were disrupted in lysis buffer: 50 mM Hepes, 150 mM NaCl, 1 mM EDTA, 1 mM EGTA, 10% glycerol, 1% Triton X-100, 10 µM $MgCl_2$, 20 mM p-nitrophenyl phosphate, 1 mM $Na_3VO_4$, 25 mM NaF, and protease inhibitor cocktail (1:25, Roche, Nutley, N.J., USA), pH 7.5. The lysates were immediately placed on ice for 10 minutes and then centrifuged for 30 min (14,000 rpm) at 4° C. Supernatants, corresponding to the cytosolic fraction, were collected, and protein concentrations were determined by the Bradford assay (BioRad, Hercules, Calif.).

Cell samples containing the cytosolic fraction (20 µg) were separated on 10% SDS-PAGE followed by immunoblotting (Gallagher et al., 2008, "Immunoblotting and immunodetection", In: "Current protocols in immunology", Coligan et al., Eds., Chapter 8: Unit 810, John Wiley & Sons, NYC, N.Y., USA). Antibodies against double phosphorylated ERK1/2 (1:5000 dilution, Sigma-Aldrich, St. Louis, Mo., USA) were detected and digitally quantified using Fuji imager (Fujifilm Life Science, Woodbridge, Conn.). Densitometric analysis was performed using ImageJ software (Collins, 2007, BioTechniques 43 (1 Suppl):25-30). The value obtained for both ERK1 and ERK2 was normalized to actin levels. The data were normalized to control.

In-Cell Western Assay for ERK Activity

Cells were grown to confluence in 96-well plates and serum-starved overnight prior to assay. Following drug treatment the media was removed and 4% paraformaldehyde in PBS was added to fix cells for 20 minutes at room temperature. Cells were then permeabilized by 0.1% Triton X-100 in PBS for 5 washes, 5 minutes per wash. LI-COR blocking buffer was added and samples were shaken on a rotator for 1 hour. Primary antibodies against phospho-ERK1/2 (Cell Signaling Technology, 1:100) were applied for 2 hours and then secondary antibodies goat anti-rabbit 800CW (1:800) were applied overnight in a cold room. Sapphire700 (LI-COR, 1:1000) and DRAQ5 (Biostatus Limited, 1:2000) were added together with the secondary antibodies for normalization. The plate was dried and then scanned using a LI-COR Odyssey Infrared Imager set at 169 µM resolution, 3 focus offset, and 4.5-6 intensity. Data were analyzed using Excel and Prism 4.0 software.

Data Analysis

βarr2-GFP aggregates were identified by a wavelet-based, Microsoft Windows-compatible computer program written in the MatLab programming environment. A program algorithm extracts from two dimensional images those pixels that generate objects of interest that fall within a predetermined range of sizes and intensities and that are embedded among widely varying local backgrounds (L. Barak, available from the Duke University GPCR Assay Bank). Concentration-effect curves for agonist-mediated receptor activation were analyzed by non-linear regression techniques using GraphPad Prism 4.0 software (GraphPad) and data were fitted to sigmoidal dose-response curves to obtain EC50 or IC50 values. Statistical analysis was performed using one-way analysis of variance (ANOVA) followed by Dunnett's post-test or two-tailed unpaired student t test. P values of <0.05 are considered significant.

Abdominal Constriction Test in Mice

Four groups of 10 male, Swiss Webster mice (30-35 g) (Ace Laboratories) were used. The animals were housed five per cage with free access to food and water. A standard light-dark cycle was maintained with a timer-regulated light period from 07.00 to 19.00 hours. The experimental procedures were approved by the Temple University Institutional Animal Care and Use Committee. Before the experiment the mice were acclimated to individual rectangular observation boxes for approximately 1 hr. They were then injected s.c. with saline or one of three doses of pamoic acid disodium (25, 50 and 100 mg/kg). Twenty min later, each mouse was challenged i.p. with 0.6% acetic acid (0.30 ml/30 g animal) and, after an additional 5 min, was observed over the following 10 min for abdominal writhing behavior.

Middle Cerebral Artery Occlusion and Reperfusion

The method to generate artery occlusion with reperfusion (MCAO/R) as described by Zhang and coworkers (Microvasc. Res. 2009, 78(1):86-94) was adapted herein. Male mice were anesthetized with an intraperitoneal injection of a 1:1 mixture of ketamine (100 mg/ml)-xylazine (20 mg/kg) at a dose of 1 ml/kg. Body temperature was maintained at 37±5° C. by a heating lamp and heating pad.

Middle cerebral artery occlusion was achieved using intraluminal filament methods. Briefly, a midline neck incision was made using an operation microscope; the right common carotid artery (CCA), external carotid artery (ECA) and internal carotid artery (ICA) were isolated. The ECA was ligated with 6-0 silk suture distal from the ICA-ECA branch and then cut distal from ligated point. Another 6-0 silk suture was tied loosely around ECA close to the origin at the CCA. A blunted 5-0 monofilament nylon suture coated with poly-L-lysine (0.1% in deionized water, Sigma Inc, St Louis Mo.) was introduced from a small incision on ECA and then advanced into the circle of Willis, and finally to the origin of the middle cerebral artery. The silk suture around the ECA stump was tied tightly to prevent bleeding and secure the nylon suture. The nylon suture was removed after 60 min of occlusion and ECA was permanently tied. Reperfusion was confirmed when pulsations were again observed in the ICA. The same surgical procedures were performed on sham animals without occlusions of the middle cerebral artery.

Preparative Example 1

Cell Line Used for Screening Studies

A prototypical U2OS osteosarcoma cell line that permanently expresses β-arrestin-GFP and N-terminal triple HA-tagged human GPR35a was used to screen ligands for agonism or antagonism against the GPR35 receptor. This GPR35-overexpressing cell line (also known as UGPR35β cells) is suitable for establishing an assay specific for screening ligands that only activate or inactivate GPR35 and not other plasma membrane receptors. Endogenous receptors are invisible to the assay because there are too few endogenous receptors of any type compared to the number of β-arrestin molecules in the cell to provide a measurable response.

U2OS cells were selected by Zeocin® and G418® antibiotic treatment to permanently overexpress the human GPR35a receptor modified with an N-terminal triple HA tag (HA-GPR35) and β-arrestin2 conjugated with Renilla-GFP (βarr-GFP). The β-arrestin-GFP fluorescence from UGPR35β cells could be imaged as green, and the receptor labeled with anti-HA antibody and co-labeled with Alexa 568 goat anti-mouse could be imaged as red.

To demonstrate the presence of receptor at the plasma membrane, live non-permeabilized UGPR35β cells permanently expressing β-arrestin-GFP and HA-GPR35a were treated with: (A) 1:1500 dilution of goat anti-mouse (GAM) antibody only, or (B) 1:400 dilution of mouse monoclonal anti-HA antibody plus 1:1500 dilution of GAM antibody.

The resulting pictures are shown in FIG. 2, wherein GFP fluorescence was excited with a fluorescein filter set (panels I and II) and Alexa568 fluorescence was excited with a rhodamine set (panels III and IV). In panels (I) and (II), the green fluorescence (seen as light gray in the black-and-white photos) confirmed the expression of β-arrestin2-GFP in the cells. In panel (III), where the cells were not treated with anti-HA antibody, no fluorescence was observed, whereas in panel (IV), where the cells were treated with anti-HA antibody, the cells showed red fluorescence (seen as mid gray in the black-and-white photos).

Example 1

Screening of Ligands for GPR35 Agonism or Antagonism

To search for more potent GPR35 ligands, U2OS cells stably co-expressing human HAGPR35a and βarr2-GFP (UGPR35β) were prepared. High content cell imaging of βarr2-GFP provides a reliable means to recognize the activation states of GPCRs (Barak et al., 1997, Mol. Pharmacol. 51(2):177-84). Upon agonist-mediated GPCR activation, β-arrestins rapidly redistribute en masse to ligand-activated plasma membrane receptors, and then the activated GPCR/arrestin complexes concentrate in clathrincoated pits and/or internal vesicles. The agonist-mediated redistribution of β-arrestin fits a sigmoid dose-response model in which the ligand affinities approximate the measured EC50s of the active compounds (Barak et al., 2003, Assay Drug Dev. Technol. 1(3):409-424; Ozawa et al., 2005, Cytometry A 65(1):69-76).

As the result of screening compounds for activity against the GPR35 receptors, pamoic acid (also known as embonic acid or 4-[(3-carboxy-2-hydroxynaphthalen-1-yl)methyl]-3-hydroxynaphthalene-2-carboxylic acid) was identified as a potent agonist of this receptor.

Figure 3A:
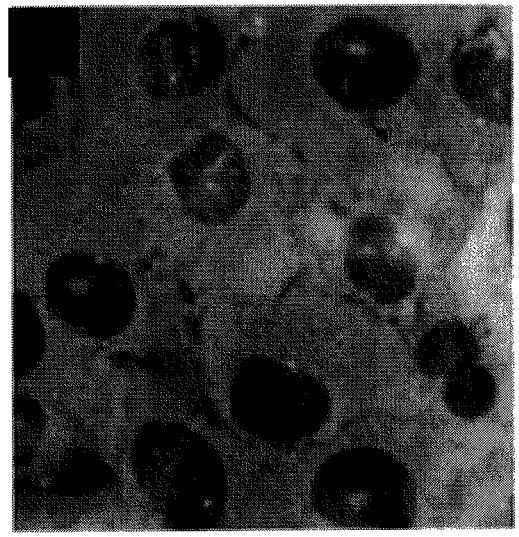
FIGS. 3A-C show fluorescence-derived images of UGPR35β cells excited with a fluorescein filter set.
Figure 3B:
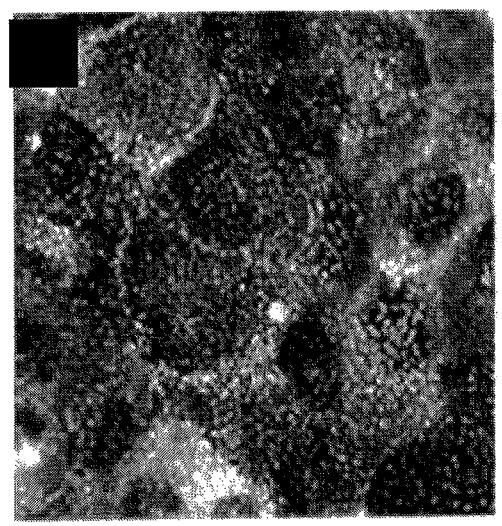
Figure 3C:
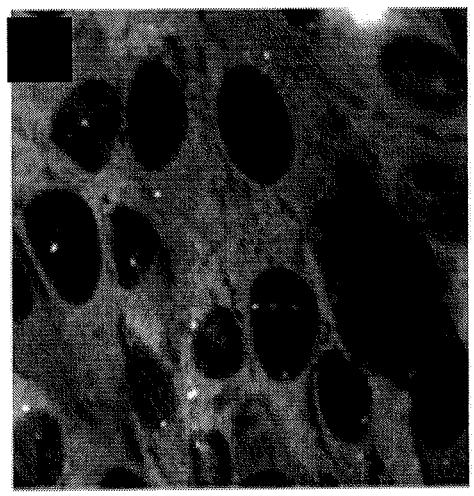

The homogeneous basal distribution of β-arrestin2-GFP fluorescence in UGPR35β cells is shown in FIG. 3A. As seen in that picture, the plasma membrane was not labeled and fluorescence was excluded from the nucleus. Addition of 1 µM of pamoic acid to the UGPR35β cells resulted in redistribution of the β-arrestin2-GFP to the cell membrane, as evidenced in FIG. 3B. In that panel, fluorescence was observed close to the cell membrane. As a control for drug specificity, 1 µM pamoic acid was added to a U2OS cell line containing β-arrestin2-GFP and overexpressed vasopressin receptor (V2R). As seen in FIG. 3C, no change in fluorescence distribution was observed, indicating a lack of responsiveness of the V2R receptor to pamoic acid.

As additional controls for drug specificity, 1 µM pamoic acid was applied to a U2OS cell line co-expressing β-arr2-GFP and CB1 cannabinoid receptors; as well as to another U2OS cell line co-expressing βarr2-GFP and GPR55 receptors; no response was observed in either cell line (data not shown).

Since GPR35 shares 30% identity with the putative cannabinoid receptor GPR55 (Guo et al., 2008, J. Pharmacol. Exp. Therap. 324(1):342-51; Johns et al., 2007, Br. J.

Pharmacol. 152(5):825-31; Ryberg et al., 2007, Br. J. Pharmacol. 152(7):1092-1101; Taniguchi et al., 2006, FEBS Lett. 580(21):5003-08), the UGPR35β cells were also treated with GPR55 ligands and a group of structurally diverse cannabinoid ligands comprised of classic, non-classic, and endogenous agonists as well as antagonists: anandamide; 2-arachidonyl-glycerol; delta-9-tetrahydrocannabinol; WIN55212-2 ((R)-(+)-[2,3-dihydro-5-methyl-3-(4-morpholinylmethyl)pyrrolo[1,2,3-de)-1,4-benzoxazin-6-yl]-1-napthalenylmethanone); CP55,940 (2-[(1R,2R,5R)-5-hydroxy-2-(3-hydroxypropyl)cyclohexyl]-5-(2-methyloctan-2-yl)phenol); AM251 (1-(2,4-dichlorophenyl)-5-(4-iodophenyl)-4-methyl-N-(1-piperidyl)pyrazole-3-carboxamide); AM4056 (1-hydroxy-1',1'-dimethylheptylhexahydrocannabinol); HU-210 ((6aR, 10aR)-9-(hydroxymethyl)-6,6-dimethyl-3-(2-methyloctan-2-yl)-6a,7,10,10a-tetrahydrobenzo[c]chromen-1-ol); O-1602 (5-methyl-4-[(1R,6R)-3-methyl-6-(1-methyethenyl)-2-cyclohexen-1-yl]-1,3-benzenediol); SR144528 (5-(4-chloro-3-methylphenyl-1-[(4-methylphenyl)methyl]-N-[(1S,2S,4R)-1,3,3-trimethylbicyclo[2.2.1]hept-2-yl]-1H-pyrazole-3-carboxamide); VCHSR1 (5-(4-chlorophenyl)-3-[(E)-2-cyclohexylethenyl]-1-(2,4-dichlorophenyl)-4-methyl-1H-pyrazole); cannabidiol; cannabinol; JWH-015 ((2-methyl-1-propyl-1H-indol-3-yl)-1-naphthalenylmethanone); PIMSR1 (5-(4-chlorophenyl)-1-(2,4-dichlorophenyl)-4-methyl-3-[(E)-piperidinoiminomethyl]-1H-pyrazole); lysophosphatidylinositol; and lysophosphatidic acid. None of the compounds at concentrations up to 30 μM activated GPR35 to produce a distribution of βarr2-GFP different from the basal state or that observed in vehicle-treated cells.

Example 2

In Vitro Assay

Concentration Response Analysis of GPR35 Agonists

Concentration response curves for β-arrestin2 aggregation were obtained for compounds of interest. For this study, UGPR35β cells were treated with different concentrations of a compound of interest and images of the cells (acquired in triplicate in three or more independent experiments) were analyzed for fluorescence. The % response for each compound at different concentrations was computed by analyzing the images for the number of translocated β-arrestin2-GFP aggregates.

Figure 4A:
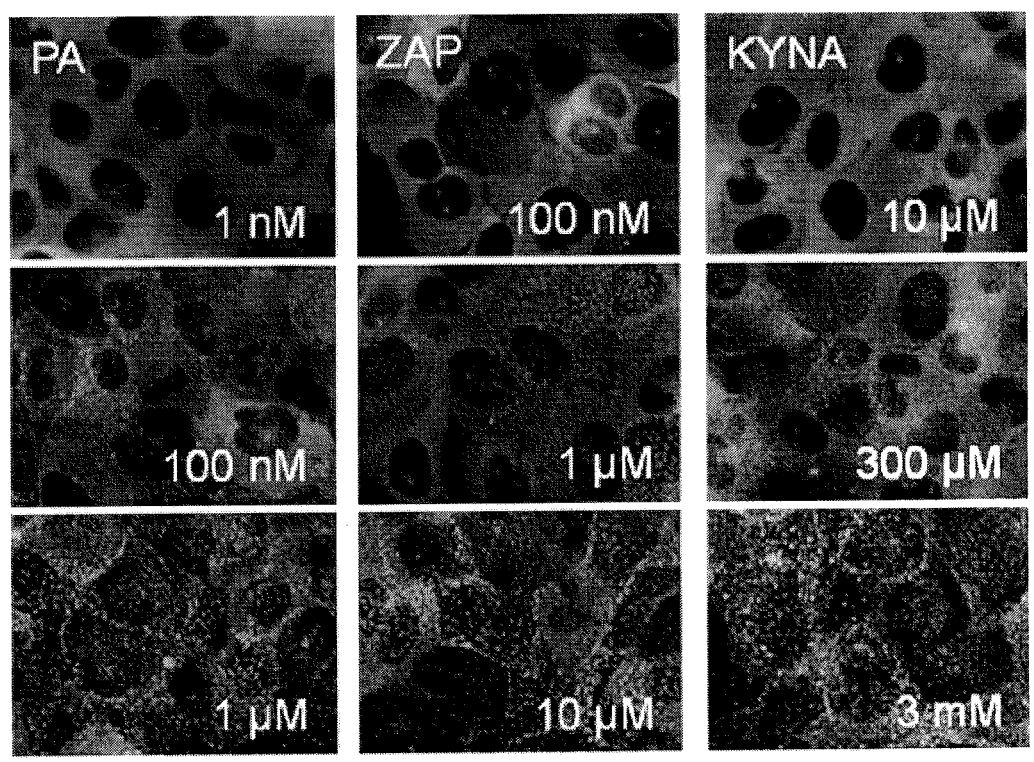
FIGS. 4A-B show the concentration response analysis for various compounds in terms of β-arrestin aggregation.
Figure 4B:
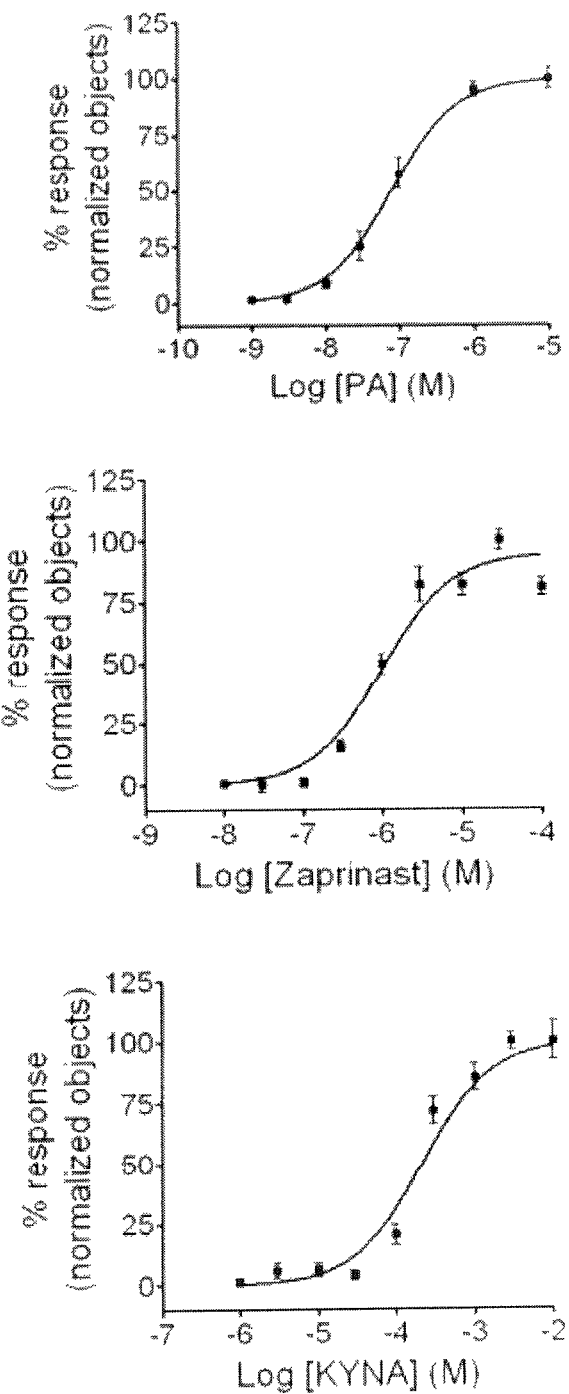

FIG. 4A shows the fluorescence-derived images obtained for each concentration of the tested compounds (pamoic acid, zaprinast and kynurenic acid). FIG. 4B shows the concentration response curves for each tested compound. Pamoic acid was very potent in this assay, with an $EC_{50}$ value of 79 μM (53 nM-117 nM): these values are the mean and 95% confidence level intervals from 4 independent experiments.

Pamoic acid was indeed significantly more potent than previously described agonists, such as zaprinast, which had an $EC_{50}$ value of 1.0 μM (0.67 μM-1.4 μM), kynurenic acid, which had an $EC_{50}$ value of 217 μM (146 μM-323 μM) and NPPB (5-nitro-2-(3-phenylpropylamino)-benzoic acid), which had an $EC_{50}$ value of 4.3 μM (data not shown).

Figure 10:
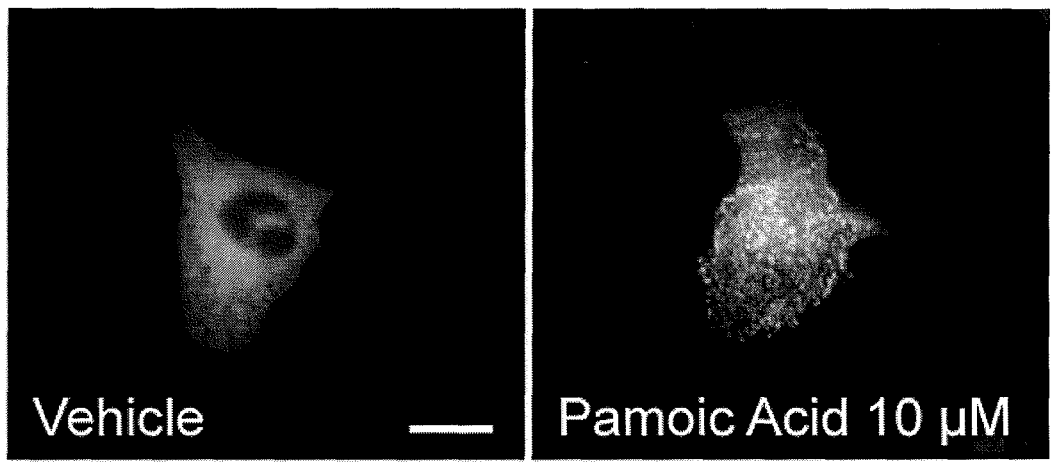
FIG. 10 shows the pamoic-acid induction of βarr2-GFP response in GPR35b-expressing U2OS cells, which were transiently transfected with GPR35b and βarr2-GFP. Scale bar, 10 μm.

Pamoic acid also induced trafficking of β-arrestin in U2OS cells co-expressing the GPR35b isoform with β-arrestin2-GFP (FIG. 10).

The $EC_{50}$ values of various compounds were determined using the concentration response curve procedure described above. The results are summarized in Table 1. Pamoic acid (1) showed the lowest $EC_{50}$ value in this assay ($EC_{50}$=79 nM). The related binaphthyl derivatives 7,7'-dibromopamoic acid (3) and 1,1'-binaphthyl-2,2'-diol-3,3'-dicarboxylic acid (4) were also found to be potent agonists ($EC_{50}$=169 nM, and $EC_{50}$=286 nM, respectively). The potent agonistic effect of oxantel pamoate (2) was found to be derived from its pamoic acid component, based on the fact that the $EC_{50}$ values for pamoic acid and oxantel pamoate were almost identical in this assay. Mononaphthyl compounds such as (7) and (8) were found to be much less potent as GPR35 agonists.

TABLE 1

$EC_{50}$ values derived from concentration response analysis in UGPR35β cells.

| Compound no. | Compound name | Structure | β-arrestin response ($EC_{50}$, nM) |
|---|---|---|---|
| 1 | pamoic acid, or 4-[(3-carboxy-2-hydroxynaphthalen-1-yl)methyl)-3-hydroxynaphthalene-2-carboxylic acid | 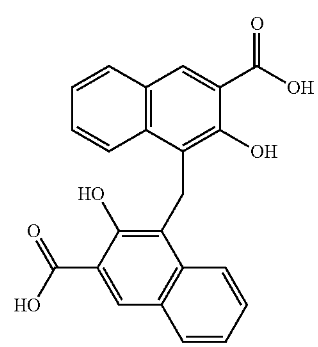 [SMILES: O=C(O)c1cc2ccccc2c(Cc2c(O)c(C(=O)O)cc3ccccc23)c1O] | 79 nM |

TABLE 1-continued

EC$_{50}$ values derived from concentration response analysis in UGPR35β cells.

| Compound no. | Compound name | Structure | β-arrestin response (EC$_{50}$, nM) |
|---|---|---|---|
| 2 | oxantel pamoate | | 91 nM |
| 3 | 7,7'-dibromo-pamoic acid | 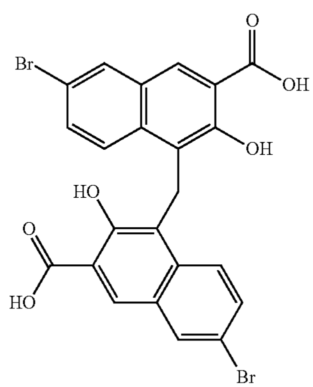 [SMILES: O=C(O)c1cc2cc(Br)ccc2c(Cc2c(O)c(C(=O)O)cc3cc(Br)ccc23)c1O] | 169 nM |
| 4 | 1,1'-binaphthyl-2,2'-diol-3,3'-dicarboxylic acid | 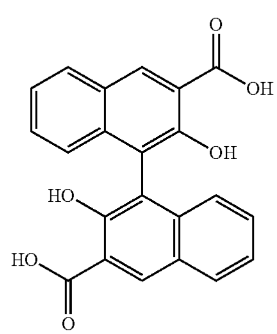 [SMILES: O=C(O)c1cc2ccccc2c(-c2c(O)c(C(=O)O)cc3ccccc23)c1O] | 286 nM |
| 5 | zaprinast, or 5-(2-propoxyphenyl)-2,3-dihydrotriazolo[4,5-d]pyrimidin-7-one | 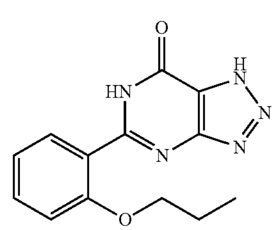 [SMILES: CCCOc1ccccc1-c1nc2nn[nH]c2c(=O)[nH]1] | 1,000 nM |

TABLE 1-continued

EC$_{50}$ values derived from concentration response analysis in UGPR35β cells.

| Compound no. | Compound name | Structure | β-arrestin response (EC$_{50}$, nM) |
|---|---|---|---|
| 6 | NPPB, or 5-Nitro-2-(3-phenylpropylamino)-benzoic acid | [structure] | 4,300 nM |
| 7 | 7-bromo-3-hydroxy-2-naphthoic acid | [structure] | 6,900 nM |
| 8 | 3-hydroxy-2-naphthoic acid | [structure] | 86,000 nM |

Example 3

In Vitro Assay

Agonist-Induced Internalization

Figure 5A:
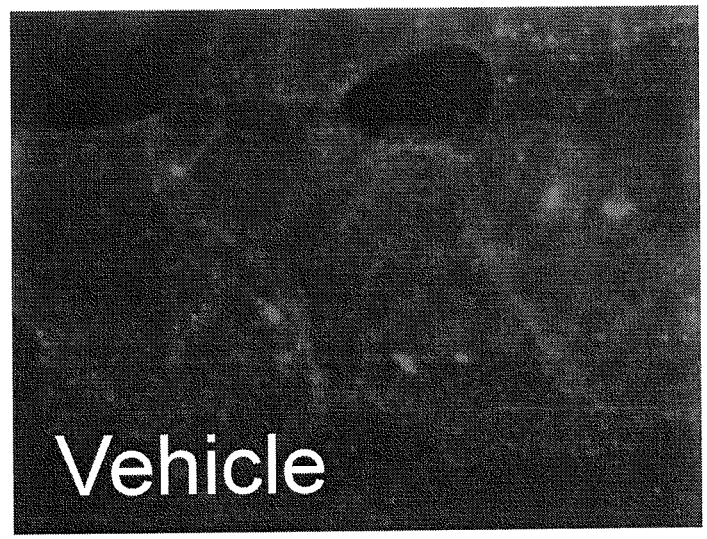
FIGS. 5A-D show the pamoic acid-induced GPR35 internalization in UGPR35β cells.
Figure 5B:
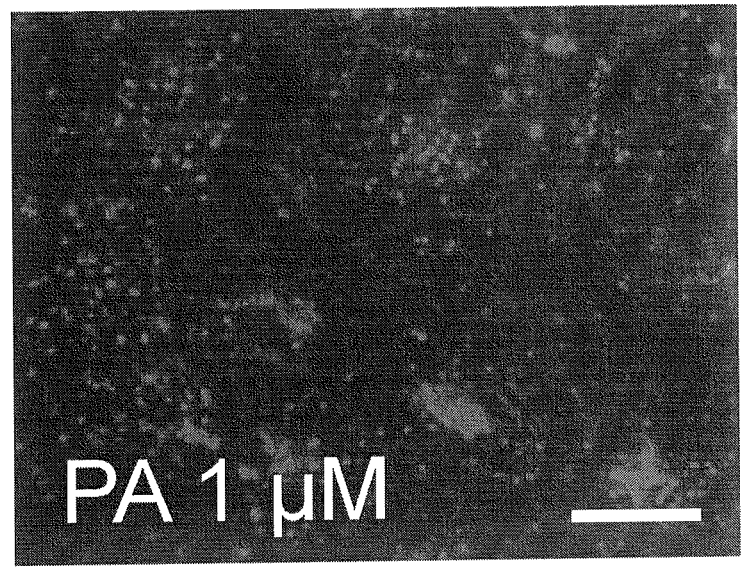
Figure 5C:
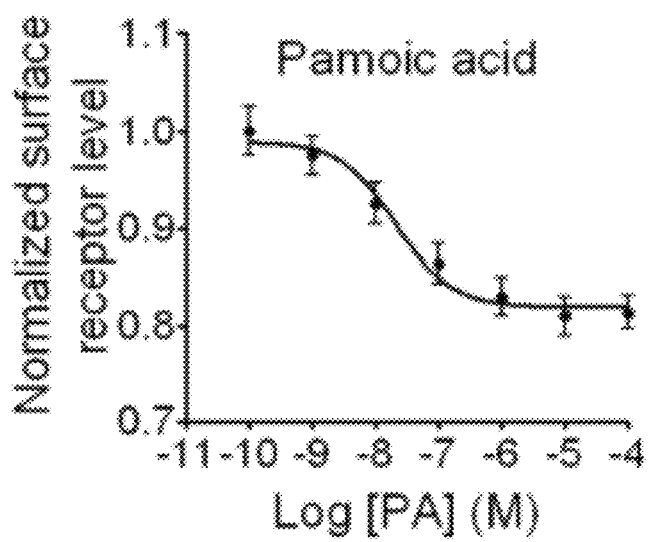
Figure 5D:
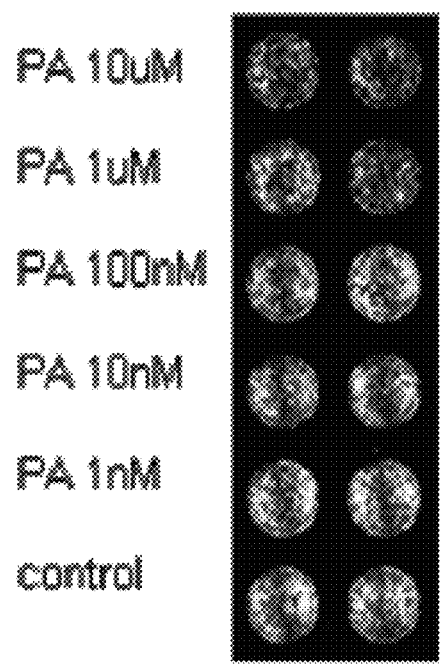

Ligand-induced GPR35 receptor internalization was evaluated by immunofluorescence, based on the loss of receptor from the cell surface due to ligand binding Immunofluorescence staining of HA-GPR35 in untreated UGPR35β cells (control) revealed that GPR35 protein was localized to the plasma membrane, as shown in FIG. 5A. Addition of 1 µM pamoic acid to the system induced translocation of GPR35 from plasma membrane to form clusters in the cytosol, as shown in FIG. 5B. On-Cell western analysis was performed using a LI-COR odyssey infra-red imager to quantify ligand potency to induce loss of cell surface receptor. For each concentration of pamoic acid, the intensity of labeling was measured using immunofluorescence. The readings were plotted against the concentrations of pamoic acid, yielding binding curves that allowed the calculation of EC$_{50}$ values. Pamoic acid induced GPR35 internalization with a (log EC$_{50}$) value of −7.447, which corresponds to EC$_{50}$=35 nM (FIG. 5C). FIG. 5D represents images from LI-COR using pamoic acid (PA) at different concentrations.

Figure 6A:
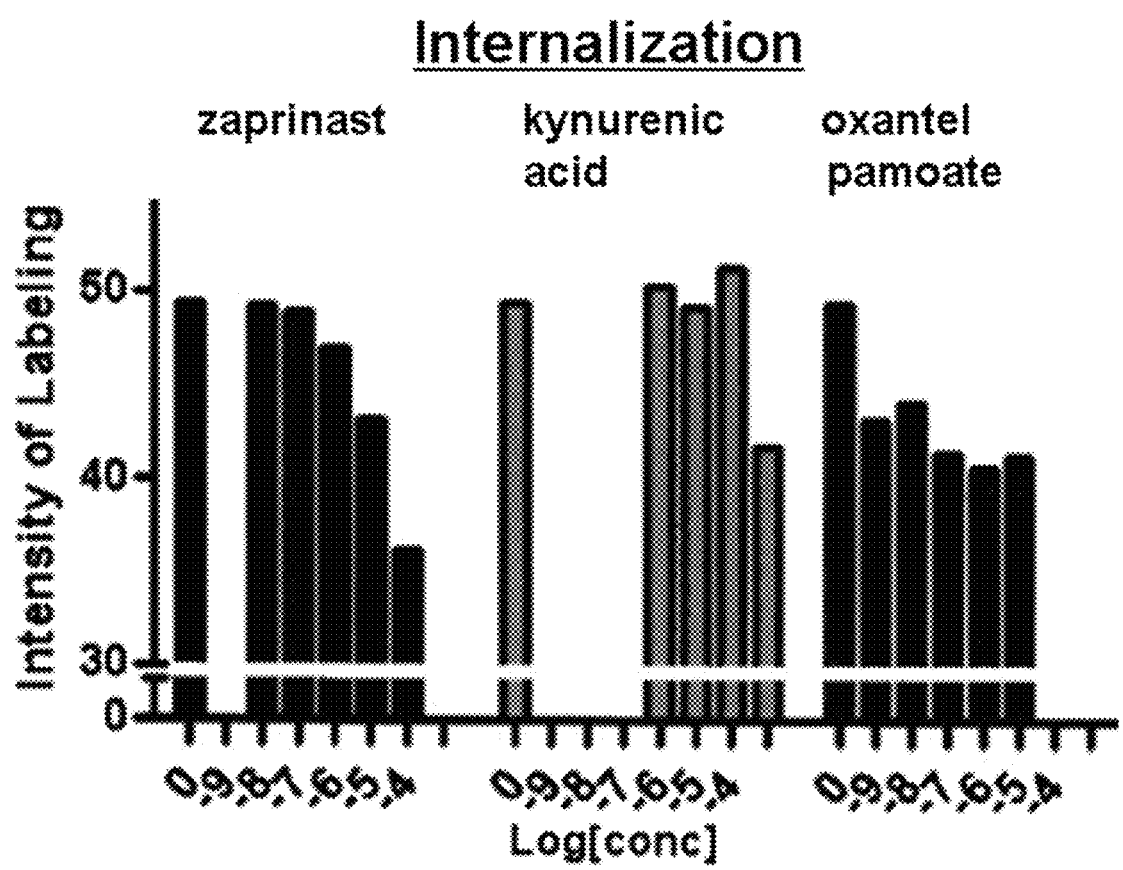
Figure 6B:
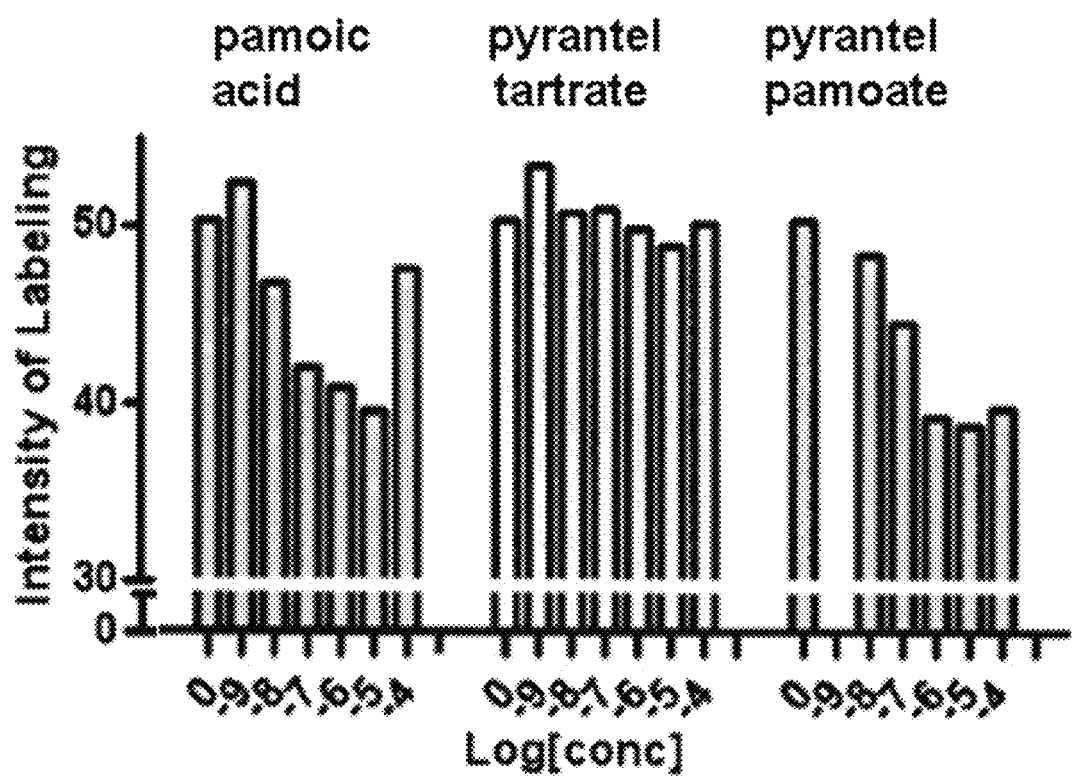
Figure 6E:
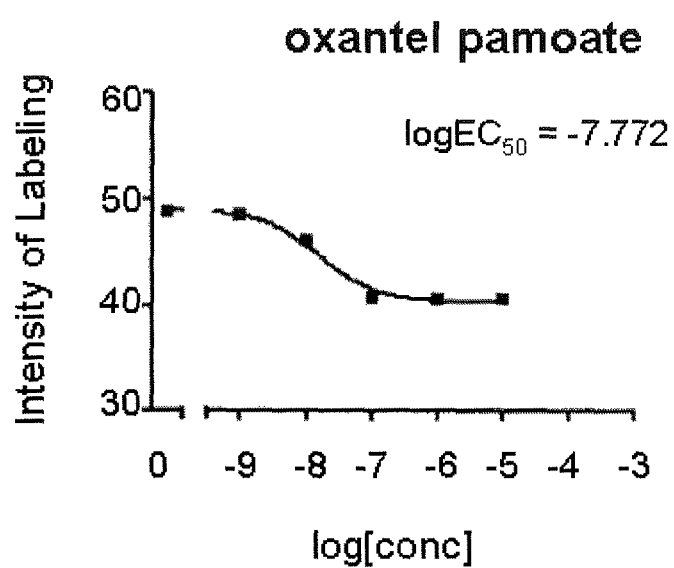

The ligand-induced receptor internalization assay was performed with other compounds of interest (FIGS. 6A-B). For each concentration of the compound of interest, the intensity of labeling was measured using immunofluorescence. The readings were plotted against the compound concentrations, yielding binding curves that allowed the calculation of EC$_{50}$ values (FIGS. 6C-E).

Zaprinast induced GPR35 internalization with a log (EC$_{50}$) value of −5.681, which corresponds to EC$_{50}$=2,084 nM. Oxantel pamoate induced GPR35 internalization with a log(EC$_{50}$) value of −7.772, which corresponds to EC$_{50}$=17 nM, a value very close to the EC$_{50}$ of pamoic acid in this assay. This observation is consistent with the conclusion that the pamoic acid component of oxantel pamoate is responsible for the agonistic activity against the GPR35 receptor. Similarly, pyrantel pamoate induced GPR35 internalization with a log(EC$_{50}$) value of −7.052 which corresponds to EC$_{50}$=89 nM, while pyrantel tartrate was inactive in this assay. This indicated that the pamoic acid component of pyrantel pamoate was responsible for the agonistic activity against GPR35.

Example 4

In Vitro Assay

Activation of ERK1/2 in UGPR35β

Figure 11A:
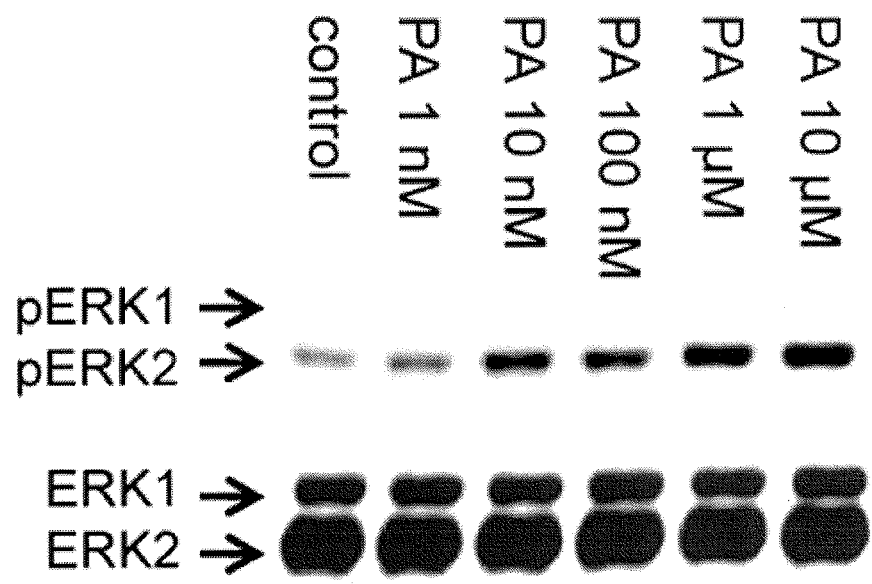
Figure 11B:
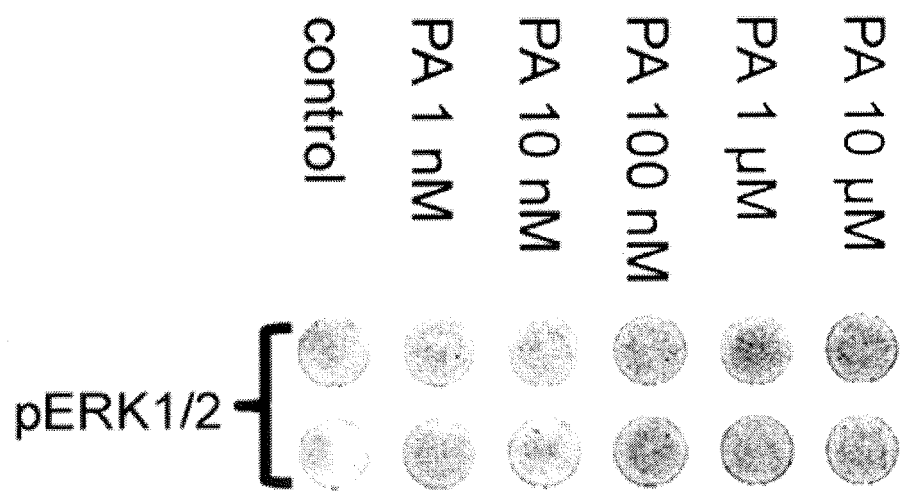

GPR35 has been implicated in malignant transformation, and the ERK/MAPK pathway is a key signaling mechanism that regulates many cellular functions such as cell growth, transformation and apoptosis (Chong et al., 2003. Cell Signal 15(5):463-69). Using Western analysis of U2OS cells expressing GPR35a receptors, GPR35 modulation of the ERK/MAPK pathway was investigated by measuring pamoic acid and zaprinast-induced phospho-ERK1/2 responsiveness. A concentration-dependent activation of ERK1/2 was observed for pamoic acid with an EC$_{50}$ of 65 nM (28-155, n=3) (FIGS. 11A-C). A five minute application of pamoic acid resulted in ERK1/2 phosphorylation and a peak effect was reached at 15 minutes. ERK1/2 phosphorylation occurred from zaprinast treatment as well with an EC$_{50}$ of 2.6 µM (1.1-6.5, n=3) (FIG. 11C). The potency of zaprinast was 40 fold lower than pamoic acid in this assay as would be predicted from the βarrestin-trafficking and internalization results. Confirmation that the activation of ERK observed with pamoic acid was occurring through induction of upstream signaling was obtained using the MEK inhibitor U0126 (1,4-diamino-2,3-dicyano-1,4-bis(2-aminophenylthio)-butadiene). Incubation of cells with 3 µM U0126 inhibited ERK1/2 activation and also abolished pamoic acid-induced ERK activation, indicating that MEK is the upstream activator of ERK1/2 for pamoic acid (data not shown).

Figure 7C:
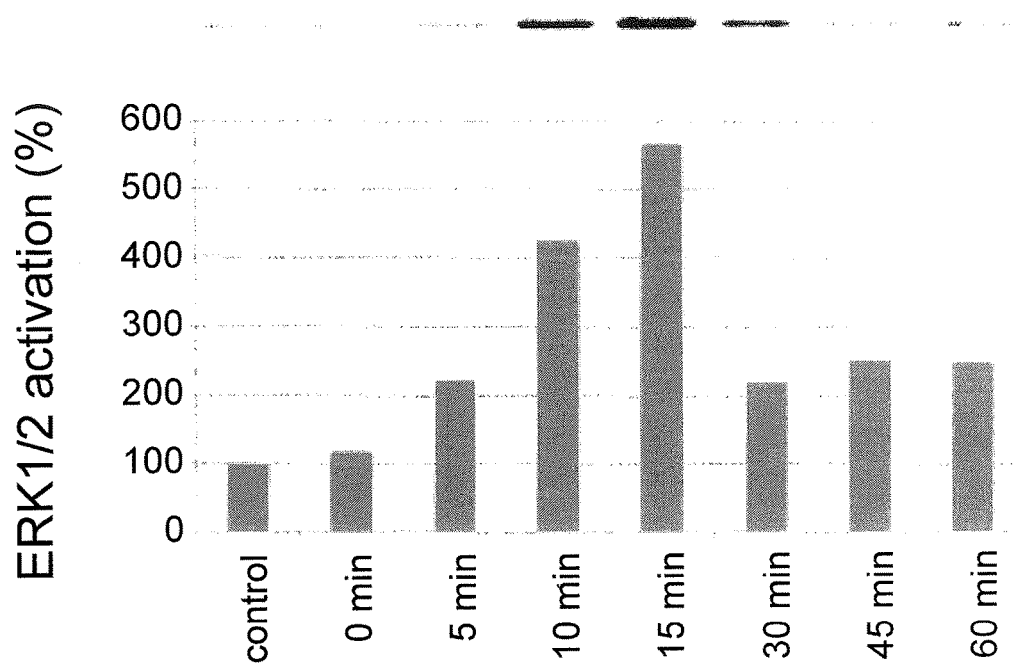

Another in vitro assay for GPR35 agonists is based on the activation/phosphorylation of ERK1/2 in UGPR35β cells. In order to determine whether pamoic acid activates ERK1/2 in UGPR35β cells, the cells were serum starved overnight and then treated with 10 μM pamoic acid in HBSS. Pronounced phosphorylation of ERK1/2 was observed in the pamoic acid treated cells compared to controls. As shown in FIG. 7A, Western blot analysis and quantitation indicated that the levels of phosphorylated ERK1 and ERK2 increased upon treatment with pamoic acid. In these studies, levels of actin were used to normalize the data. FIG. 7B represents the time-dependent effect of pamoic acid in pERK1/2 levels as determined by In-Cell Western analysis using LI-COR infrared imager. Quantitation of data was normalized to cell number. The result of this study indicated that phosphorylation of ERK1/2 in UGPR35β may be used as an in vitro assay to evaluate GPR35 agonists. As shown in FIG. 7C, the extent of ERK1/2 activation detected in this assay is a function of the incubation time of the compound of interest with the cells. In this particular example, the % ERK1/2 activation reached a maximum at 15 minutes incubation time and decreased subsequently.

Example 5

In Vivo Assay

Antinociception

The acetic acid writhing test (Porreca et al., 1987, J. Pharmacol. Exp. Ther. 240 (3):890-894) was used to evaluate pamoic acid as an antinociceptic agent.

Four groups of 10 male Swiss Webster mice (30-35 g) were acclimated to individual rectangular observation boxes for approximately 1 hour, and then injected subcutaneously with saline or one of three doses of disodium pamoate (25, 50 and 100 mg/kg). Twenty minutes later, each mouse was challenged i.p. with 0.6% acetic acid. Five minutes after the challenge, each mouse was observed over the following 10 min for writhing behavior. The mean number of writhes associated with the saline-control group was 21±1. Writhing was decreased in a dose-related manner after 25, 50 and 100 mg/kg of disodium pamoate (14±2, 11±2 and 0.4±0.2, respectively).

Figure 8:
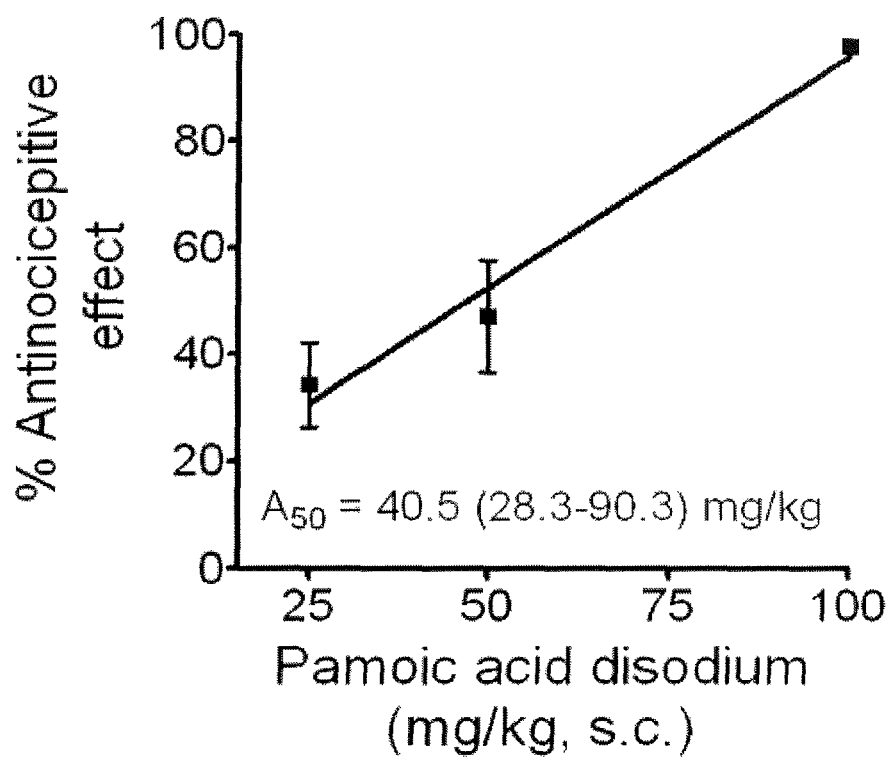
FIG. 8 corresponds to a graph depicting the dose-responsive antinociceptive effect of pamoic acid in the acetic acid writhing in mice. Doses of disodium pamoate (given subcutaneously) are shown in mg/kg.

The relationship between dose of disodium pamoate and mean % antinociceptive effect±s.e.m. is shown in FIG. 8. Pamoic acid injected subcutaneously demonstrated a dose-responsive antinociceptive effect in mice, with a subcutaneous dose of 40.5 mg/kg (28.3-90.3 mg/kg, 95% CL) causing 50% antinociception and essentially complete antinociception being associated with a dose of 100 mg/kg.

Example 6

Investigation of Neuroprotection in a Mouse Model of Stroke

Middle cerebral artery occlusion with reperfusion (MCAO/R) was performed in male mice as a model for neuroprotection in animals afflicted with stroke. MCAO/R was performed according to published procedures (Zhang et al., 2009, Microvasc. Res. 78 (1):86-94). The animals were divided in two groups. In the first group (n=5), the animals were administered disodium pamoate one hour prior to reperfusion. In the second group (n=3, control), the animals were not administered any test compound before reperfusion.

Cerebral infarction volume was measured 24 hours after MCAO/R. The animals were euthanized with an overdose of pentobarbital (200 mg/kg i.p.) 24 hours after MCAO and the brains were removed, and chilled on ice for 10 min to slightly harden the tissue. Five 2-mm coronal sections were cut using a mouse brain matrix (Zivic lab, Pittsburgh, Pa., USA). The brain sections were placed in 2% triphenyltetrazolium chloride (TTC) (Sigma Inc, St Louis, Mo., USA) dissolved in saline and stained for 20 minutes at 37° C. in the dark. The brain sections were then fixed in 4% paraformaldehyde at 4° C. for 24 hours, and the anterior and caudal face of each section was scanned by a flatbed color scanner (Microtek Inc, Carson, Calif., USA). The resulting images were captured as JPEG files and analyzed with NIH image software. The infarct volumes were corrected for brain edema/swelling: the hemispheric infarct volume in each section was calculated by subtracting the area of normal TTC stained tissue in the hemisphere ipsilateral to the ligation, from the contralateral non-ischemic area to generate the infarct fraction (%).

Figure 9:
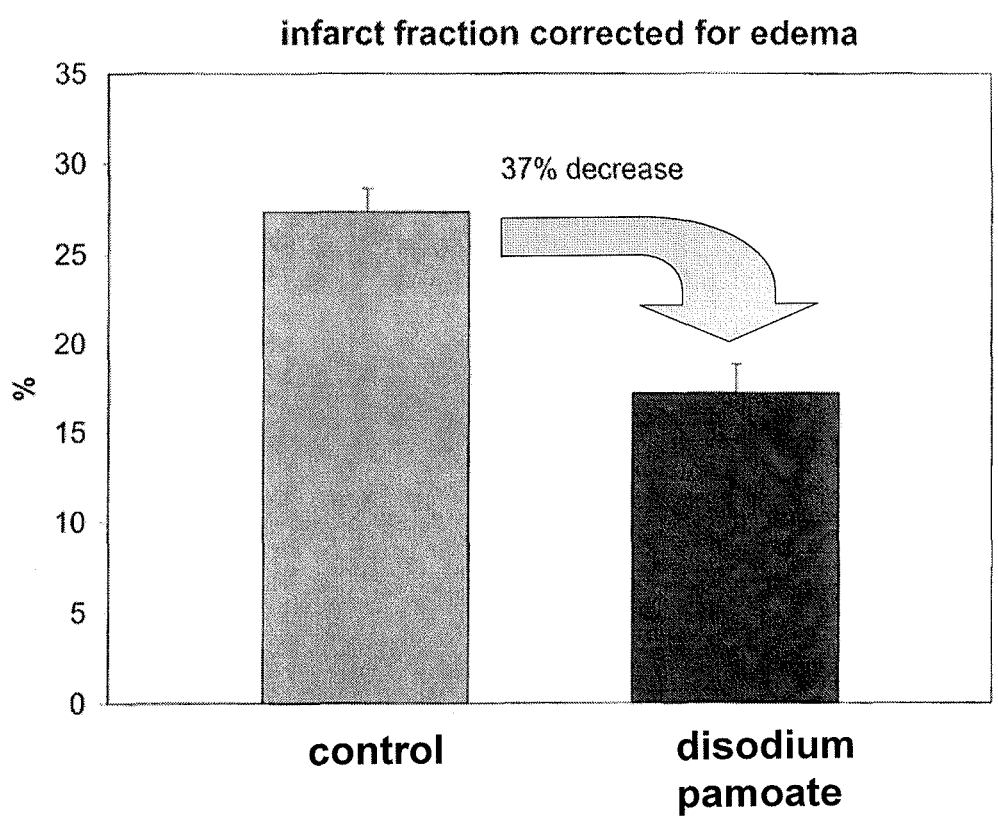
FIG. 9 corresponds to a bar graph indicating the infarction percentage observed in the male mice model of middle cerebral artery occlusion with reperfusion, upon administration of the disodium salt of pamoic acid vs untreated animals.

Corrected infarction percentages for animals treated with disodium pamoate and control animals are shown in FIG. 9. Control animals showed an infarction percentage of about 27%, and the animals treated with disodium pamoate showed an infarction percentage of about 17%. Administration of disodium pamoate in this assay thus caused a reduction of about 37% in infarction percentage in this model.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:

1. A method of providing antinociception to a subject in need thereof, said method comprising administering to said subject a therapeutically effective amount of a compound of Formula (I):

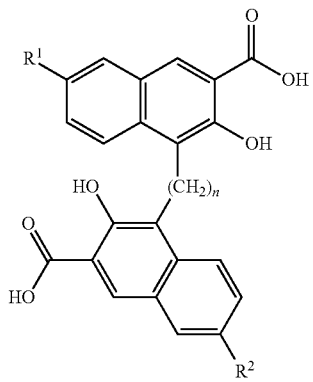

or a pharmaceutically acceptable salt thereof, wherein:

$R^1$ and $R^2$ are independently H, F, Cl, Br or I; and, n is 0 or 1;

wherein said pharmaceutically acceptable salt comprises a cationic counterion which itself does not provide therapeutically useful antinociception to said subject.

2. The method of claim 1, wherein said compound of Formula (I) is pamoic acid, or a pharmaceutically acceptable salt thereof.

3. The method of claim 1, wherein said compound of Formula (I) is 7,7'-dibromo-pamoic acid, or a pharmaceutically acceptable salt thereof.

4. The method of claim 1, wherein said compound of Formula (I) is 1,1'-binaphthyl-2,2'-diol-3,3'-dicarboxylic acid, or a pharmaceutically acceptable salt thereof.

5. The method according to claim 1, wherein the subject is a human being.

6. The method according to claim 2, wherein the compound is disodium pamoate.

* * * * *

SEQUENCE LISTING

<160> NUMBER OF SEQ ID NOS: 4

<210> SEQ ID NO 1
<211> LENGTH: 309
<212> TYPE: PRT
<213> ORGANISM: Homo sapiens

<400> SEQUENCE: 1

Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60

Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Ala Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285

Leu Ala Val Ala Pro Arg Ala Lys Ala His Lys Ser Gln Asp Ser Leu
    290                 295                 300

Cys Val Thr Leu Ala
305

<210> SEQ ID NO 2
<211> LENGTH: 340
<212> TYPE: PRT
<213> ORGANISM: Homo sapiens

<400> SEQUENCE: 2

Met Leu Ser Gly Ser Arg Ala Val Pro Thr Pro His Arg Gly Ser Glu
1               5                   10                  15

Glu Leu Leu Lys Tyr Met Leu His Ser Pro Cys Val Ser Leu Thr Met
            20                  25                  30

Asn Gly Thr Tyr Asn Thr Cys Gly Ser Ser Asp Leu Thr Trp Pro Pro
        35                  40                  45

Ala Ile Lys Leu Gly Phe Tyr Ala Tyr Leu Gly Val Leu Leu Val Leu

```
            50                  55                  60
Gly Leu Leu Leu Asn Ser Leu Ala Leu Trp Val Phe Cys Cys Arg Met
 65                  70                  75                  80

Gln Gln Trp Thr Glu Thr Arg Ile Tyr Met Thr Asn Leu Ala Val Ala
                 85                  90                  95

Asp Leu Cys Leu Leu Cys Thr Leu Pro Phe Val Leu His Ser Leu Arg
             100                 105                 110

Asp Thr Ser Asp Thr Pro Leu Cys Gln Leu Ser Gln Gly Ile Tyr Leu
         115                 120                 125

Thr Asn Arg Tyr Met Ser Ile Ser Leu Val Thr Ala Ile Ala Val Asp
     130                 135                 140

Arg Tyr Val Ala Val Arg His Pro Leu Arg Ala Arg Gly Leu Arg Ser
145                 150                 155                 160

Pro Arg Gln Ala Ala Ala Val Cys Ala Val Leu Trp Val Leu Val Ile
                165                 170                 175

Gly Ser Leu Val Ala Arg Trp Leu Leu Gly Ile Gln Glu Gly Gly Phe
            180                 185                 190

Cys Phe Arg Ser Thr Arg His Asn Phe Asn Ser Met Ala Phe Pro Leu
        195                 200                 205

Leu Gly Phe Tyr Leu Pro Leu Ala Val Val Val Phe Cys Ser Leu Lys
    210                 215                 220

Val Val Thr Ala Leu Ala Gln Arg Pro Thr Asp Val Gly Gln Ala
225                 230                 235                 240

Glu Ala Thr Arg Lys Ala Ala Arg Met Val Trp Ala Asn Leu Leu Val
                245                 250                 255

Phe Val Val Cys Phe Leu Pro Leu His Val Gly Leu Thr Val Arg Leu
            260                 265                 270

Ala Val Gly Trp Asn Ala Cys Ala Leu Leu Glu Thr Ile Arg Arg Ala
        275                 280                 285

Leu Tyr Ile Thr Ser Lys Leu Ser Asp Ala Asn Cys Cys Leu Asp Ala
    290                 295                 300

Ile Cys Tyr Tyr Tyr Met Ala Lys Glu Phe Gln Glu Ala Ser Ala Leu
305                 310                 315                 320

Ala Val Ala Pro Arg Ala Lys Ala His Lys Ser Gln Asp Ser Leu Cys
                325                 330                 335

Val Thr Leu Ala
            340

<210> SEQ ID NO 3
<211> LENGTH: 309
<212> TYPE: PRT
<213> ORGANISM: Homo sapiens

<400> SEQUENCE: 3

Met Asn Gly Thr Tyr Asn Thr Cys Gly Ser Ser Asp Leu Thr Trp Pro
 1                   5                  10                  15

Pro Ala Ile Lys Leu Gly Phe Tyr Ala Tyr Leu Gly Val Leu Leu Val
                 20                  25                  30

Leu Gly Leu Leu Leu Asn Ser Leu Ala Leu Trp Val Phe Cys Cys Arg
             35                  40                  45

Met Gln Gln Trp Thr Glu Thr Arg Ile Tyr Met Thr Asn Leu Ala Val
         50                  55                  60

Ala Asp Leu Cys Leu Leu Cys Thr Leu Pro Phe Val Leu His Ser Leu
 65                  70                  75                  80
```

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
            115                 120                 125

Ser Pro Arg Gln Ala Ala Ala Val Cys Ala Val Leu Trp Val Leu Val
130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Arg Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
            195                 200                 205

Ala Glu Ala Thr Arg Lys Ala Ala Arg Met Val Trp Ala Asn Leu Leu
210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
            275                 280                 285

Leu Ala Val Ala Pro Arg Ala Lys Ala His Lys Ser Gln Asp Ser Leu
290                 295                 300

Cys Val Thr Leu Ala
305

<210> SEQ ID NO 4
<211> LENGTH: 309
<212> TYPE: PRT
<213> ORGANISM: Homo sapiens

<400> SEQUENCE: 4

Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60

Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
            115                 120                 125

Ser Pro Arg Gln Ala Ala Ala Val Cys Ala Val Leu Trp Val Leu Val
130                 135                 140

```
Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Ala Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
            245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285

Leu Ala Val Ala Pro Ser Ala Lys Ala His Lys Ser Gln Asp Ser Leu
    290                 295                 300

Cys Val Thr Leu Ala
305
```